United States Patent
Lapointe et al.

(10) Patent No.: US 10,941,449 B2
(45) Date of Patent: Mar. 9, 2021

(54) METHOD OF SCREENING FOR COLORECTAL CANCER

(71) Applicant: CLINICAL GENOMICS PTY. LTD., New South Wales (AU)

(72) Inventors: Lawrence Charles Lapointe, New South Wales (AU); Susanne K. Pedersen, New South Wales (AU); Rohan Baker, New South Wales (AU); Snigdha Gaur, New South Wales (AU); Melissa Thomas, New South Wales (AU)

(73) Assignee: CLINICAL GENOMICS PTY. LTD., New South Wales (AU)

( * ) Notice: Subject to any disclaimer, the term of this patent is extended or adjusted under 35 U.S.C. 154(b) by 873 days.

(21) Appl. No.: 14/401,157

(22) PCT Filed: May 17, 2013

(86) PCT No.: PCT/AU2013/000519
§ 371 (c)(1),
(2) Date: Nov. 14, 2014

(87) PCT Pub. No.: WO2013/170314
PCT Pub. Date: Nov. 21, 2013

(65) Prior Publication Data
US 2015/0152505 A1 Jun. 4, 2015

Related U.S. Application Data

(60) Provisional application No. 61/648,821, filed on May 18, 2012.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57446* (2013.01); *C12Q 2523/125* (2013.01); *C12Q 2600/112* (2013.01); *C12Q 2600/154* (2013.01); *G01N 2800/06* (2013.01); *G01N 2800/50* (2013.01)

(58) Field of Classification Search
None
See application file for complete search history.

(56) References Cited

U.S. PATENT DOCUMENTS

2010/0167940 A1    7/2010    Feinberg et al.

FOREIGN PATENT DOCUMENTS

WO    2012034170 A1    3/2012
WO    2013026104 A1    2/2013

OTHER PUBLICATIONS

Martinelli et al. IKZF1 (Ikaros) Deletions in BCR-ABL1-Positive Acute Lynphoblastic Leukemia Are Associated With Short Disease-Free Survival and High Rate of Cumulative Incidence of Relapse: A GIMEMA AL WP Report Journal of Clinical Oncology vol. 27, pp. 5202-5207 (2009).*
Grady et al. Detection of Aberrantly Methylated hMLH1 Promoter DNA in the Serum of Patients with Microsatellite Unstable Colon Cancer Cancer Research vol. 61, pp. 900-902 (Year: 2001).*
Hibi et al. Molecular Detection of Genetic Alterations in the Serum of Colorectal Cancer Patients Cancer Research vol. 58, pp. 1405-1407 (Year: 1998).*
Warren et al. Septin 9 methylated DNA is a sensitive and specific blood test for colorectal cancer BMC Medicine vol. 9, article 133 (Year: 2011).*
De Wijkersloth et al. Study protocol: population screening for colorectal cancer by colonoscopy or CT colonography: a randomized controlled trial BMC Gastroenterology vol. 10, article 47 (Year: 2010).*
Fisher et al. Dukes Claddification Revisited Cancer vol. 64, pp. 2354-2360 (Year: 1989).*
Labianca et al. Primary colon cancder: ESMO Clinical Practice Guidelines for diagnosis, adjuvant treatment and follow-up annals of Oncology vol. 21, supplement 5 pp. v70-v77 (Year: 2010).*
Cassinotti et al., "DNA methylation patterns in blood of patients with colorectal cancer and adenomatous colorectal polyps", International Journal of Cancer 131.5 (2012): 1153-1157, 5 pages.
Coppedè, "Epigenetic biomarkers of colorectal cancer: focus on DNA methylation", Cancer letters 342.2 (2014): 238-247, 10 pages.
European Patent Application No. EP13790927.1, "Extended European Search Report", dated May 3, 2016, 19 pages.
Kang, "Four molecular subtypes of colorectal cancer and their precursor lesions", Archives of pathology & laboratory medicine 135.6 (2011): 698-703, 6 pages.
Lao et al., "Epigenetics and colorectal cancer", Nature Reviews Gastroenterology and Hepatology 8.12 (2011): 686-700, 15 pages.
Øster et al., "Identification and validation of highly frequent CpG island hypermethylation in colorectal adenomas and carcinomas", International journal of cancer 129.12 (2011): 2855-2866, 12 pages.

(Continued)

*Primary Examiner* — John S Brusca
(74) *Attorney, Agent, or Firm* — Knobbe, Martens, Olson & Bear LLP

(57) ABSTRACT

The present invention relates generally to a method of determining one or more probabilities of respective classifications of a neoplasm into one or more neoplastic categories. More particularly, the present invention relates to a method of determining the probability of classification of a large intestine neoplasm into one or more categories selected from adenoma, stage I, stage II, stage III or stage IV by screening for changes to the methylation levels of a panel of gene markers, including BCAT1, IKZF1, IRF4, GRASP and/or CAHM. The method of the present invention is useful in a range of applications including, but not limited to, those relating to the diagnosis and/or monitoring of colorectal neoplasms, such as colorectal adenocarcinosis.

12 Claims, 4 Drawing Sheets
(2 of 4 Drawing Sheet(s) Filed in Color)
Specification includes a Sequence Listing.

(56) References Cited

OTHER PUBLICATIONS

Adorjan et al., "Tumour class prediction and discovery by microarray-based DNA methylation analysis", Nucleic Acids Research 30: e21, 2002.

Ammerpohl et al., "Hunting for the 5th base: Techniques for analyzing DNA methylation", Biochimica et Biophysica Acta (BBA)-General Subjects 1790.9 (2009): 847-862.

Beaucage et al., "Deoxynucleoside Phosphoramidites—A New Class of Key Intermediates for Deoxypolynucleotide Synthesis", Tetrahedron Letters, vol. 22, No. 20, 1981, pp. 1859-1862.

Caruthers et al., "Chemical Synthesis of Deoxyoligonucleotides by the Phosphoramidite Method", Methods in Enzymology, vol. 154, Feb. 1987, pp. 287-313.

Chen et al., "Template-directed dye-terminator incorporation (TDI) assay:a homogeneous DNA diagnostic method based on fluorescence energy transfer", Nucleic Acids Res. 25:347-353 (1997).

Clark et al., "DNA methylation: bisulphite modification and analysis", Nat Protoc 2006; 1: 2353-64, (2006).

Cottrell et al., "A real-time PCR assay for DNA-methylation using methylation-specific blockers", Nucleic acids research 32.1: e10-e10 (2003).

Degraves et al., "High-Sensitivity Quantitative PCR Platform", BioTechniques 34(1): 106-115, (2003).

Deiman et al., "Characteristics and applications of nucleic acid sequence-based amplification (NASBA)", Molecular biotechnology 20(2): 163-179, (2002).

Devos et al., "Circulating methylated SEPT9 DNA in plasma is a biomarker for colorectal cancer", Clinical chemistry 55(7): 1337-1346 (2009).

Eads et al., "CpG island hypermethylation in human colorectal tumors is not associated with DNA methyltransferase overexpression", Cancer research 59.10: 2302-2306, (1999).

Eads et al., "MethyLight: a high-throughput assay to measure DNA methylation", Nucleic acids research 28.8: e32 (2002).

Egholm et al., "Peptide nucleic acids (PNA). Oligonucleotide analogs with an achiral peptide backbone", Journal of the American Chemical Society 114.5: 1895-1897 (1992).

Egholm et al., "PNA hybridizes to complementary oligonucleotides obeying the Watson-Crick hydrogen-bonding rules", Nature 365: 566-568 (1993).

Fodor et al., "Light-Directed, Spatially Addressable Parallel Chemical Synthesis", Science, Feb. 15, 1991, 251, 767-773.

Frommer et al., "A genomic sequencing protocol that yields a positive display of 5-methylcytosine residues in DNA strands", Proc. Natl. Acad. Sci. USA 89, 1827-1831 (1992).

Gibson et al., "A Novel Method for Real Time Quantitative RT-PCR", Genome Research, 1996, 6; 995-1001.

Golub et al., "Molecular Classification of Cancer: Class Discovery and Class Prediction by Gene Expression Monitoring", Science, vol. 286, Oct. 15, 1999, pp. 531-537.

Gonzalgo et al., "Identification and characterization of differentially methylated regions of genomic DNA by methylation-sensitive arbitrarily primed PCR", Cancer Research 57.4: 594-599 (1997).

Gonzalgo et al., "Rapid quantitation of methylation differences at specific sites using methylation-sensitive single nucleotide primer extension (Ms-SNuPE)", Nucleic Acids Research, 25(12):2529-2531 (1997).

Gregory et al., "Analysis of chromatin in limited numbers of cells: a PCR-SSCP based assay of allele-specific nuclease sensitivity", Nucleic Acids Res., 27, e32i-e32iv, (1999).

Herman et al., "Methylation-specific PCR: a novel PCR assay for methylation status of CpG islands", Proceedings of the National Academy of Sciences of the United States of America, 93(18):9821-9826 (1996).

Holland et al., "Detection of specific polymerase chain reaction product by utilizing the 5'-3' exonuclease activity of thermos aquaticus DNA polymerase", Proceeding of the National Academy of Sciences, vol. 88, Aug. 1991, pp. 7276-7280.

Kawai et al., "Comparison of DNA methylation patterns among mouse cell lines by restriction landmark genomic scanning", Molecular and Cellular Biology 14.11: 7421-7427, (1994).

Kristensen et al., "PCR-based methods for detecting single-locus DNA methylation biomarkers in cancer diagnostics, prognostics, and response to treatment", Clinical chemistry 55.8: 1471-1483, (2009).

Kuppuswamy et al., "Single nucleotide primer extension to detect genetic diseases: experimental application to hemophilia B (factor IX) and cystic fibrosis genes", Proceedings of the National Academy of Sciences 88.4: 1143-1147, (1991).

Landegren et al., "Reading bits of genetic information: methods for single-nucleotide polymorphism analysis", Genome Research 8.8: 769-776, (1998).

Lee et al., "Allelic Discrimination by Nick-Translation PCR with Fluorogenic Probes", Nucleic Acids Research, 1993, vol. 21, No. 16, pp. 3761-3766.

Markowitz et al., "Molecular Origins of Cancer: Molecular Basis of Colorectal Cancer", The New England journal of medicine, 361(25):2449-2460, (2009).

Messing, "New M13 vectors for cloning", Methods in Enzymology, 101: 20-78 (1983).

Mhlanga et al., "Using molecular beacons to detect single-nucleotide polymorphisms with real-time PCR", Methods 25.4 (2001): 463-471.

Narang et al., "Improved phosphotriester method for the synthesis of gene fragments", Methods in enzymology 68 (1978): 90-98.

Nielsen et al., "Synthesis of 2'-O, 3'-C-linked bicyclic nucleosides and bicyclic oligonucleotides", Journal of the Chemical Society, Perkin Transactions 1 22 (1997): 3423-3434.

Olek et al., "The preimplantation ontogeny of the H19 Methylation imprint", Nat. Genet. 17(3): 275-6 (1997).

Orum et al., "Detection of the factor V Leiden mutation by direct allele-specific hybridization of PCR amplicons to photoimmobilized locked nucleic acids", Clin. Chem. 45:1898-1905, 1999.

Orum et al., "Single base pair mutation analysis by PNA directed PCR clamping", Nucleic Acids Res., 1993, 21(23):5332-5336.

Rand et al., "Bisulphite differential denaturation PCR for analysis of DNA methylation", Epigenetics 1.2 (2006): 94-100.

Rand et al., "Headloop suppression PCR and its application to selective amplification of methylated DNA sequences", Nucleic acids research 33.14 (2005): e127-e127.

Rein et al., "Identifying 5-methylcytosine and related modifications in DNA genomes", Nucleic acids research 26.10 (1998): 2255-2264.

Sadri et al., "Rapid analysis of DNA methylation using new restriction enzyme sites created by bisulfite modification", Nucleic acids research 24.24 (1996): 5058-5059.

Shames et al., "Methods for detecting DNA methylation in tumors: from bench to bedside", Cancer letters 251.2 (2007): 187-198.

Simeonov et al., "Single nucleotide polymorphism genotyping using short, fluorescently labeled locked nucleic acid (LNA) probes and fluorescence polarization detection", Nucleic Acids Research, 30(17):1-5, 2002.

Singer-Sam et al., "A quantitative HpaII-PCR assay to measure methylation of DNA from small numbers of cells", Nucl. Acids Res. 18:687, 1990.

Singer-Sam et al., "A sensitive, quantitative assay for measurement of allele-specific transcripts differing by a single nucleotide", PCR methods and applications 1.3 (1992): 160.

Singh et al., "Universality of LNA-mediated high-affinity nucleic acid recognition", Chemical Communications 12 (1998):1247-1248.

Southern et al., "Analyzing and Comparing Nucleic Acid Sequences by Hybridization to Arrays of Oligonucleotides: Evaluation Using Experimental Models", Genomics, 1992, 13, 1008-1017.

Szabó et al., "Allele-specific expression and total expression levels of imprinted genes during early mouse development: implications for imprinting mechanisms", Genes & development 9.24 (1995): 3097-3108.

Toyota et al., "Identification of differentially methylated sequences in colorectal cancer by methylated CpG island amplification", Cancer research 59.10 (1999): 2307-2312.

(56) References Cited

OTHER PUBLICATIONS

Uhlmann et al., "Evaluation of a Potential Epigenetic Biomarker by Quantitative Methyl-single Nucleotide Polymorphism Analysis", Electrophoresis, vol. 23, Issue 24, Dec. 2002, pp. 4072-4079.

Worm et al., "In-tube DNA methylation profiling by fluorescence melting curve analysis", Clinical chemistry 47.7 (2001): 1183-1189.

Xiong et al., "COBRA: a sensitive and quantitative DNA methylation assay", Nucleic acids research 25.12 (1997): 2532-2534.

International Application No. PCT/AU2013/000519, International Search Report dated Jun. 28, 2013.

Javierre, B.M. et al.: 'Long Rang Epigenetic Silencing Associates with Deregulation of Ikaros Targets in Colorectal Cancer Cells' Molecular Cancer Research vol. 9, No. 8, 2011, pp. 1139-1151.

Kibriya, M.G. et al.: 'A genome-wide DNA methylation study in colorectal carcinoma' BMC Medical Genomics vol. 4, No. 50, 2011, pp. 1-16.

Øster, B. et al.: 'Identification and validation of highly frequent CpG island hypermethylation in colorectal adenomas and carcinomas' International Journal of Cancer vol. 129, No. 12, 2011, pp. 2855-2866.

EP13790927.1, "Partial Supplementary European Search Report", dated Jan. 5, 2016, 10 pages.

Javierre et al., "Long-range epigenetic silencing associates with deregulation of Ikaros targets in colorectal cancer cells", Molecular Cancer Research, vol. 9, No. 8, Jul. 7, 2011, pp. 1139-1151.

Pedersen et al., "CAHM, a long non-coding RNA gene hypermethylated in colorectal neoplasia", Epigenetics, vol. 9, Issue 8, Aug. 2014, pp. 1071-1082.

Pedersen et al., "Discovery and Validation of a Novel DNA Methylation Biomarker for Colorectal Cancer With Application to Blood Testing", Gastroenterology, vol. 142, Issue 5, Supplement 1, May 2012, p. S-33.

* cited by examiner

METHOD OF SCREENING FOR COLORECTAL CANCER

PRIOR RELATED APPLICATIONS

This application is a U.S. national phase patent application under 35 U.S.C. 371 of International Patent Application No. PCT/AU2013/000519, filed May 17, 2013, which claims the benefit of priority to the U.S. Provisional Application No. 61/648,821, filed May 18, 2012, each of which is incorporated herein by reference in its entirety.

FIELD OF THE INVENTION

The present invention relates generally to a method of classifying a large intestine neoplasm and, in particular, classifying a colorectal neoplasm in a mammal. The present invention more specifically provides a method for assessing the probability that a large intestine neoplasm is a premalignant neoplasm, an early stage malignant neoplasm or a late stage malignant neoplasm. The method of the present invention is based on screening for modulation in the DNA methylation levels of one or more gene markers in blood samples from said mammal.

BACKGROUND OF THE INVENTION

Colorectal cancer includes cancerous growths in the colon, rectum and appendix. With 655,000 deaths worldwide per year, it is the fourth most common form of cancer in the United States, and the third leading cause of cancer-related deaths in the Western world. Colorectal cancers arise from adenomatous polyps in the colon. These mushroom-shaped growths are usually benign, but some develop into cancer over time. Localized colon cancer is usually diagnosed through colonoscopy.

Invasive cancers that are confined within the wall of the colon (Stage I and II) are curable with surgery. If untreated, they spread to regional lymph nodes (stage III), where up to 73% are curable by surgery and chemotherapy. Cancer that metastasizes to distant sites (stage IV) is usually not curable, although chemotherapy can extend survival, and in rare cases, surgery and chemotherapy together have seen patients through to a cure (Markowitz and Bertagnolli, 2009, *N. Engl. J. Med.* 361(25): 2449-60). Radiation is used with rectal cancer.

Colorectal cancer is preceded by adenomas. Adenomas are benign tumours, or neoplasms, of epithelial origin which are derived from glandular tissue or exhibit clearly defined glandular structures. Some adenomas show recognisable tissue elements, such as fibrous tissue (fibroadenomas) and epithelial structure, while others, such as bronchial adenomas, produce active compounds that might give rise to clinical syndromes.

Adenomas may progress to become an invasive neoplasm, and are then termed adenocarcinomas. Accordingly, adenÔcarcinomas are defined as malignant epithelial tumours arising from glandular structures, which are constituent parts of many organs of the body. The term adenocarcinoma is also applied to tumours showing a glandular growth pattern. These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both mucinous and cystadenocarcinoma.

Adenomas in different organs behave differently. In general, the overall chance of carcinoma being present within an adenoma (i.e., a focus of cancer having developed within a benign lesion) is approximately 5%. However, this is related to size of an adenoma. For instance, in the large bowel (colon and rectum specifically), occurrence of a cancer within an adenoma is rare in adenomas of less than 1 centimetre. Such a development is estimated at 40 to 50% in adenomas which are greater than 4 centimetres and show certain histopathological change such as villous change, or high grade dysplasia. Adenomas with higher degrees of dysplasia have a higher incidence of carcinoma. In any given colorectal adenoma, the predictors of the presence of cancer now or the future occurrence of cancer in the organ include size (especially greater than 9 mm), degree of change from tubular to villous morphology, presence of high grade dysplasia and the morphological change described as "serrated adenoma". In any given individual, the additional features of increasing age, familial occurrence of colorectal adenoma or cancer, male gender or multiplicity of adenomas, predict a future increased risk for cancer in the organ—so-called risk factors for cancer. Except for the presence of adenomas and its size, none of these is objectively defined, and all those other than number and size are subject to observer error and to confusion as to precise definition of the feature in question. Because such factors can be difficult to assess and define, their value as predictors of current or future risk for cancer is imprecise.

Once a sporadic adenoma has developed, the chance of a new adenoma occurring is approximately 30% within 26 months.

The symptoms of colorectal cancer depend on the location of tumour in the bowel, and whether it has metastasised. Unfortunately, many of the symptoms may occur in other diseases as well, and hence symptoms may not be conclusively diagnostic of colorectal cancer.

Local symptoms are more likely if the tumour is located closer to the anus. There may be a change in bowel habit (new-onset constipation or diarrhea in the absence of another cause), a feeling of incomplete defecation, and reduction in diameter of stools. Tenesmus and change in stool shape are both characteristic of rectal cancer. Lower gastrointestinal bleeding, including the passage of bright red blood in the stool, may indicate colorectal cancer, as may the increased presence of mucus. Melena, black stool with a tarry appearance, normally occurs in upper gastrointestinal bleeding (such as from a duodenal ulcer), but is sometimes encountered in colorectal cancer when the disease is located in the beginning of the large bowel.

A tumour that is large enough to fill the entire lumen of the bowel may cause bowel obstruction. This situation is characterized by constipation, abdominal pain, abdominal distension and vomiting. This occasionally leads to the obstructed and distended bowel perforating and causing peritonitis.

Certain local effects of colorectal cancer occur when the disease has become more advanced. A large tumour is more likely to be noticed on feeling the abdomen, and it may be noticed by a doctor on physical examination. The disease may invade other organs, and may cause blood or air in the urine or vaginal discharge.

If a tumour has caused chronic occult bleeding, iron deficiency anaemia may occur. This may be experienced as fatigue, palpitations and noticed as pallor. Colorectal cancer may also lead to weight loss, generally due to a decreased appetite.

More unusual constitutional symptoms are an unexplained fever and one of several paraneoplastic syndromes. The most common paraneoplastic syndrome is thrombosis, usually deep vein thrombosis.

Colorectal cancer most commonly spreads to the liver. This may go unnoticed, but large deposits in the liver may cause jaundice and abdominal pain (due to stretching of the capsule). If the tumour deposit obstructs the bile duct, the jaundice may be accompanied by other features of biliary obstruction, such as pale stools.

Colorectal cancer can take many years to develop and early detection of colorectal cancer greatly improves the prognosis. Even modest efforts to implement colorectal cancer screening methods can result in a drop in cancer deaths. Despite this, colorectal cancer screening rates remain low.

In addition to screening for the onset of a colorectal neoplasm, determining the stage or grade of a neoplasm is also extremely valuable since this provides a patient with the possibility of better tailored treatment regimen and potentially a significantly better prognosis. Currently, staging of large intestine neoplasms is an invasive procedure since it requires the harvesting of a tissue specimen which is histologically analysed.

The most commonly used staging system for colorectal cancer is that of the American Joint Committee on Cancer (AJCC), sometimes also known as the TNM system. The TNM system describes 3 key pieces of information:

T describes how far the main (primary) tumour has grown through the layers of the intestine and whether it has grown into nearby areas. These layers, from the inner to the outer, include:
   The inner lining (mucosa)
   A thin muscle layer (muscularis mucosa)
   The fibrous tissue beneath this muscle layer (submucosa)
   A thick muscle layer (muscularis propria) that contracts to force the contents of the intestines along
   The thin, outermost layers of connective tissue (subserosa and serosa) that cover most of the colon but not the rectum N describes the extent of spread to nearby (regional) lymph nodes, and, if so, how many lymph nodes are involved.
   Nx: No description of lymph node involvement is possible because of incomplete information.
   N0: No cancer in nearby lymph nodes.
   N1a: Cancer cells are found in 1 nearby lymph node.
   N1b: Cancer cells are found in 2 to 3 nearby lymph nodes.
   N1c: Small deposits of cancer cells are found in areas of fat near lymph nodes, but not in the lymph nodes themselves.
   N2a: Cancer cells are found in 4 to 6 nearby lymph nodes.
   N2b: Cancer cells are found in 7 or more nearby lymph nodes.

M indicates whether the cancer has metastasized.
   M0: No distant spread is seen.
   M1a: The cancer has spread to 1 distant organ or set of distant lymph nodes.
   M1b: The cancer has spread to more than 1 distant organ or set of distant lymph nodes, or it has spread to distant parts of the peritoneum (the lining of the abdominal cavity).
   Numbers or letters appear after T, N, and M to provide more details about each of these factors. The numbers 0 through 4 indicate increasing severity. The letter X means "cannot be assessed because the information is not available."

T Categories for Colorectal Cancer
   T categories of colorectal cancer describe the extent of spread through the layers that form the wall of the colon and rectum.

Stage Grouping
   Once a person's T, N, and M categories have been determined, usually after surgery, this information is combined in a process called stage grouping. The stage is expressed in Roman numerals from stage I (the least advanced) to stage IV (the most advanced). Some stages are subdivided with letters.

Stage 0
   Tis, N0, M0 The cancer is in the earliest stage. It has not grown beyond the inner layer (mucosa) of the colon or rectum. This stage is also known as carcinoma in situ or intramucosal carcinoma.

Stage I
   T1-T2, N0, M0: The cancer has grown through the muscularis mucosa into the submucosa (T1) or it may also have grown into the muscularis propria (T2). It has not spread to nearby, lymph nodes or distant sites.

Stage IIA
   T3, N0, M0: The cancer has grown into the outermost layers of the colon or rectum but has not gone through them. It has not reached nearby organs. It has not yet spread to the nearby lymph nodes or distant sites.

Stage IIB
   T4a, N0, M0: The cancer has grown through the wall of the colon or rectum but has not grown into other nearby tissues or organs. It has not yet spread to the nearby lymph nodes or distant sites.

Stage IIC
   T4b, N0, M0: The cancer has grown through the wall of the colon or rectum and is attached to or has grown into other nearby tissues or organs. It has not yet spread to the nearby lymph nodes or distant sites.

Stage IIIA
   One of the following applies.
   T1-T2, N1, M0: The cancer has grown through the mucosa into the submucosa (T1) or it may also have grown into the muscularis propria (T2). It has spread to 1 to 3 nearby lymph nodes (N1a/N1b) or into areas of fat near the lymph nodes but not the nodes themselves (N1c). It has not spread to distant sites.
   T1, N2a, M0: The cancer has grown through the mucosa into the submucosa. It has spread to 4 to 6 nearby lymph nodes. It has not spread to distant sites.

Stage IIIB
   One of the following applies.
   T3-T4a, N1, M0: The cancer has grown into the outermost layers of the colon or rectum (T3) or through the visceral peritoneum (T4a) but has not reached nearby organs. It has spread to 1 to 3 nearby lymph nodes (N1a/N1 b) or into areas of fat near the lymph nodes but not the nodes themselves (N1c). It has not spread to distant sites.
   T2-T3, N2a, M0: The cancer has grown into the muscularis propria (T2) or into the outermost layers of the colon or rectum (T3). It has spread to 4 to 6 nearby lymph nodes. It has not spread to distant sites.

T1-T2, N2b, M0: The cancer has grown through the mucosa into the submucosa (T1) or it may also have grown into the muscularis propria (T2): It has spread to 7 or more nearby lymph nodes. It has not spread to distant sites.

Stage IIIC

One of the following applies.

T4a, N2a, M0: The cancer has grown through the wall of the colon or rectum (including the visceral peritoneum) but has not reached nearby organs. It has spread to 4 to 6 nearby lymph nodes. It has not spread to distant sites.

T3-T4a, N2b, M0: The cancer has grown into the outermost layers of the colon or rectum (T3) or through the visceral peritoneum (T4a) but has not reached nearby organs. It has spread to 7 or more nearby lymph nodes. It has not spread to distant sites.

T4b, N1-N2, M0: The cancer has grown through the wall of the colon or rectum and is attached to or has grown into other nearby tissues or organs. It has spread to 1 or more nearby lymph nodes or into areas of fat near the lymph nodes. It has not spread to distant sites.

Stage IVA

Any T, Any N, M1a: The cancer may or may not have grown through the wall of the colon or rectum, and it may or may not have spread to nearby lymph nodes. It has spread to 1 distant organ (such as the liver or lung) or set of lymph nodes.

Stage IVB

Any T, Any N, M1b: The cancer may or may not have grown through the wall of the colon or rectum, and it may or may not have spread to nearby lymph nodes. It has spread to more than 1 distant organ (such as the liver or lung) or set of lymph nodes, or it has spread to distant parts of the peritoneum (the lining of the abdominal cavity).

Another factor that can affect the outlook for survival is the grade of the cancer. Grade is a description of how closely the cancer resembles normal colorectal tissue when looked at under a microscope.

The scale used for grading colorectal cancers goes from G1 (where the cancer looks much like normal colorectal tissue) to G4 (where the cancer looks very abnormal). The grades G2 and G3 fall somewhere in between. The grade is often simplified as either "low-grade" (G1 or G2) or "high-grade" (G3 or G4). Low-grade cancers tend to grow and spread more slowly than high-grade cancers.

In the context of large intestine neoplasms, the histological analysis of tissue specimens is both relatively slow and highly invasive. Due to its invasiveness, it is also not a procedure which one would want to perform repeatedly. The development of a means to reliably and routinely assess a patient to determine whether an identified neoplasm is premalignant (e.g., adenoma), early stage or late stage (e.g., metastatic) is highly desirable if it can be performed quickly and repeatedly, since this would enable decisions in relation to treatment regimes to be made and implemented more accurately. It would also enable ongoing monitoring to be performed during a treatment regime, such as in the context of treating an adenoma or early stage cancer, to assess transition to a more advanced stage without the need to perform invasive biopsies. This would also enable more, flexibility in terms of adapting treatment regimes to reflect changes to the stage of a neoplasm.

In work leading up to the present invention, it has been determined that a panel of gene markers which are known to be diagnostic of large intestine neoplasms can, in fact, also provide valuable information in relation to the classification of a neoplasm. Specifically, whereas the level of increase in the methylation of the DNA of these gene markers is similar in most biological samples, irrespective of how advanced the neoplasm is, when assessed in a blood-derived sample, such as plasma, there is found an increase in the level of methylation as the stage of the neoplasm becomes more advanced.

This finding has therefore now provided a means to assess the probability that a given neoplasm is premalignant, early stage malignant, or late stage malignant. This information in relation to the classification of the neoplasm can then inform the development of the therapeutic treatment and ongoing monitoring which is appropriate for the patient. Importantly, particularly in the context of premalignant or early stage malignant neoplasms, it provides a means for non-invasive ongoing monitoring. The method of the present invention can be performed either after initial diagnosis, or may itself form part of the screening of patients presenting for initial diagnosis but where, in addition to the diagnostic result, there is also provided classification information.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

A method of determining one or more probabilities of respective classifications of a large intestine neoplasm in an individual, said method comprising assessing the methylation status of a DNA region selected from:

(i) the region, including 2 kb upstream of the transcription start site, defined by at least one of Hg19 coordinates:
  (1) chr12:24962958 . . . 25102393
  (2) chr7:50344378 . . . 50472798
  (3) chr6:391739 . . . 411443;
  (4) chr12:52400748 . . . 52409671; and
  (5) chr6:163834097 . . . 163834982; or
(ii) the gene region, including 2 kb upstream of at least one of:

| (1) BCAT1 | (2) IKZF1 | (3) IRF4 | (4) GRASP and | (5) CAHM |
|---|---|---|---|---| in a blood-derived sample from said individual, wherein a level of methylation of at least one of the DNA regions of group (i) and/or (ii) relative to corresponding measured levels of methylation from a population of individuals with known neoplastic categories of corresponding large intestine neoplasms is used to determine one or more probabilities of respective classifications of said large intestine neoplasm of said individual into one or more neoplastic categories selected from adenoma, stage I, stage II, stage III, and stage IV categories or into one or more aggregates of fewer than five of said neoplastic categories.

In one embodiment, the method is directed to determining one or more probabilities of respective classifications of said large intestine neoplasms of said individual into one or more aggregates of fewer than five of said neoplastic categories.

The method may further include using said level of methylation for said individual to determine a probability that said large intestine of said individual would be classified as non-neoplastic, based on comparison of said level of methylation relative to said corresponding measured levels of methylation and to further corresponding measured levels of methylation from a further population of individuals whose large intestines were classified as non-neoplastic.

The subregions which have been determined to exhibit particular utility are listed below with reference to the gene and chromosomal region within which they are found:
(1) BCAT1 subregions chr12:25101992-25102093 (SEQ ID NO:1 or the corresponding minus strand) and chr12:25101909-25101995 (SEQ ID NO:2 or the corresponding minus strand)
(2) IKZF1 subregions: chr7:50343867-50343961 (SEQ ID NO:3 or the corresponding minus strand) and chr7:50343804-5033895 (SEQ ID NO:4 or the corresponding minus strand)
(3) IRF4 subregions chr6:392036-392145 (SEQ ID NO:5 or the corresponding minus strand)
(4) GRASP subregions: chr12:52399672-52399922, chr12:52400821-52401051 (SEQ ID NO:6 or the corresponding minus strand), chr12:52401407-52401664 (SEQ ID NO:7 or the corresponding minus strand) chr12:52400866-52400973 and Chr12:52401107-52401664.
(5) CAHM subregions: chr6:163834295-163834500 (SEQ ID NO:8 or the corresponding minus strand), chr6:163834621-163834906 chr6:163834393-163834455 and chr6:163834393-163834519.

Without limiting the present invention to any one theory or mode of action, the skilled person may screen one or more subregions for each gene marker.

To the extent that the method of the present invention includes analysing the methylation of BCAT1, the subject residues:

| | | | |
|---|---|---|---|
| chr12:25101998 | chr12:25102003 | chr12:25102006 | chr12:25102009 |
| chr12:25102017 | chr12:25102022 | chr12:25102039 | chr12:25102048 |
| chr12:25102050 | chr12:25102053 | chr12:25102061 | chr12:25102063 |
| chr12:25102071 | chrl12:25101921 | chr12:25101934 | chr12:25101943 |
| chr12:25101951 | chr12:25101962 | chr12:25101964 | chr12:25101970 | or a corresponding cytosine at position n+1 on the opposite DNA strand.

To the extent that the method of the present invention includes analysing the methylation of GRASP, the subject residues are:

| | | | |
|---|---|---|---|
| chr12:52399713 | chr12:52399731 | chr12:52399749 | chr12:52399783 |
| chr12:52399796 | chr12:52399808 | chr12:52399823 | chr12:52399835 |
| chr12:52399891 | | | |
| chrl 2:52400847 | chr12:52400850 | chr12:52400859 | chr12:52400866 |
| chr12:52400869 | chr12:52400873 | chr12:52400881 | chr12:52400886 |
| chr12:52400893 | chr12:52400895 | chr12:52400899 | chr12:52400902 |
| chr12:52400907 | chr12:52400913 | chr12:52400919 | chr12:52400932 |
| chr12:52400938 | chr12:52400958 | chr12:52400962 | chr12:52400971 |
| chr12:52400973 | chr12:52400976 | chr12:52400998 | chr12:52401008 |
| chr12:52401010 | chr12:52401012 | chr12:52401016 | chr12:52401019 |
| chr12:52401025 | chr12:52401041 | chr12:52401044 | chr12:52401053 |
| chr12:52401060 | chr12:52401064 | chr12:52401092 | chr12:52401118 |
| chr12:52401438 | chr12:52401448 | chr12:52401460 | chr12:52401465 |
| chr12:52401474 | chr12:52401477 | chr12:52401479 | chr12:52401483 |
| chr12:52401504 | chr12:52401514 | chr12:52401523 | chr12:52401540 |
| chr12:52401553 | chr12:52401576 | chr12:52401588 | chr12:52401595 |
| chr12:52401599 | chr12:52401604 | chr12:52401606 | chr12:52401634 |
| chr12:52401640 | chr12:52401644 | chr12:52401659 | |
| chr12:52401160 | chr12:52401165 | chr12:52401174 | chr12:52401177 |
| chr12:52401179 | chr12:52401183 | chr12:52401204 | chr12:52401215 |
| chr12:52401223 | chr12:52401240 | chr12:52401253 | chr12:52401288 |
| chr12:52401295 | chr12:52401299 | chr12:52401304 | chr12:52401334 |
| chr12:52401340 | chr12:52401344 | chr12:52401359 | | or a corresponding cytosine at position n+1 on the opposite DNA strand.

To the extent that the method of the present invention includes analysing the methylation of CAHM, the subject residues are:

| | | |
|---|---|---|
| chr6:163834330 | chr6:163834332 | chr6:163834357 |
| chr6:163834373 | chr6:163834384 | chr6:163834390 |
| chr6:163834392 | chr6:163834406 | chr6:163834412 |
| chr6:163834419 | chr6:163834443 | chr6:163834448 |
| chr6:163834452 | chr6:163834464 | chr6:163834483 |
| chr6:163834653 | chr6:163834660 | chr6:163834672 |
| chr6:163834675 | chr6:163834678 | chr6:163834681 |
| chr6:163834815 | chr6:163834824 | chr6:163834835 |
| chr6:163834840 | chr6:163834853 | chr6:163834855 |
| chr6:163834858 | chr6:163834863 | chr6:163834869 |
| chr6:163834872 | | | or a corresponding cytosine at position n+1 on the opposite DNA strand.

To the extent that the method of the present invention includes analysing the methylation of IKZF1, the subject residues are:

| | | |
|---|---|---|
| chr7:50343869 | chr7:50343872 | chr7:50343883 |
| chr7:50343889 | chr7:50343890 | chr7:50343897 |
| chr7:50343907 | chr7:50343909 | chr7:50343914 |
| chr7:50343934 | chr7:50343939 | chr7:50343950 |
| chr7:50343959 | chr7:50343805 | chr7:50343822 |
| chr7:50343824 | chr7:50343826 | chr7:50343829 |
| chr7:50343831 | chr7:50343833 | chr7:50343838 |
| chr7:50343847 | chr7:50343850 | chr7:50343858 |
| chr7:50343864 | chr7:50343869 | chr7:50343872 |
| chr7:50343890 | | | or a corresponding cytosine at position n+1 on the opposite DNA strand.

To the extent that the method of the present invention includes analysing the methylation of IRF4, the subject residues are:

| | | |
|---|---|---|
| chr6:392036 | chr6:392047 | chr6:392049 |
| chr6:392057 | chr6:392060 | chr6:392066 |
| chr6:392080 | chr6:392094 | chr6:392102 |
| chr6:392131 | | | or a corresponding cytosine at position n+1 on the opposite DNA strand.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
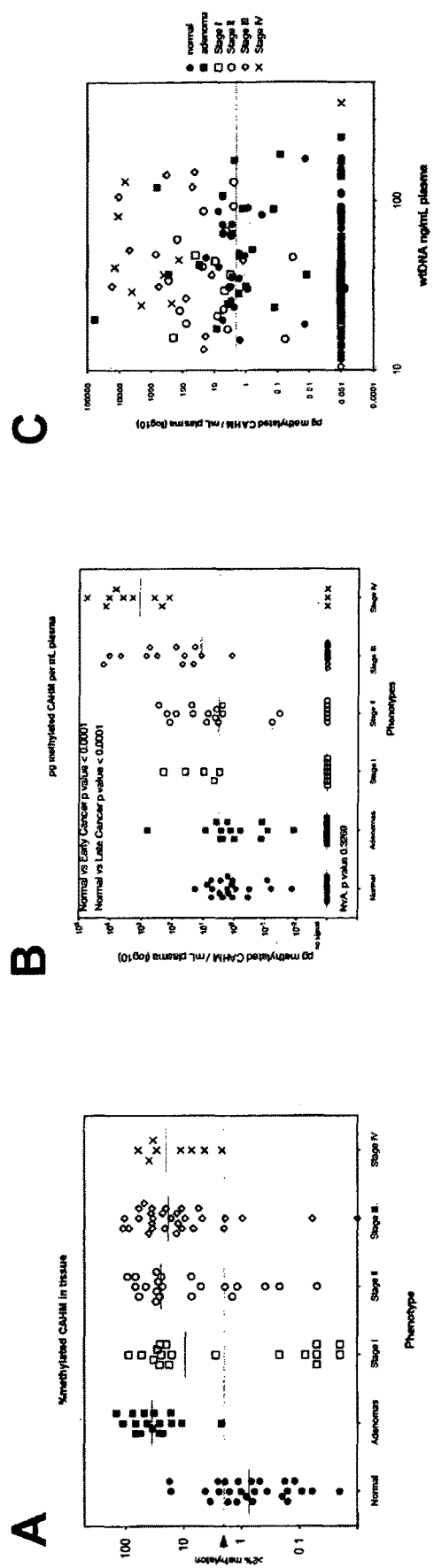
FIG. 1. Measurement of CAHM methylation levels in tissue and blood plasma specimens.
A: The levels of methylated CAHM in colorectal tissue specimens including normals (n=26, solid circles), adenomas (n=17, solid squares), Stage I (n=20, open squares), Stage II (n=21, open circles), Stage III (n=30, open diamonds) and Stage IV (n=8, crosses) were measured using the methylation specific CAHM assay described in M&M on 15 ng of bisulfite converted DNA extracted from 122 tissue specimens (Left figure). The signal output was converted to a mass/well using a calibration curve. Data is given as the % methylated CAHM measured in 15 ng of total bisulfite converted tissue DNA per reaction. Data are mean values of triplicate. B: The levels of methylated CAHM was measured in the equivalent of triplicate analysis of 0.5 mL plasma from colonoscopy-confirmed patients including normals (n=74, solid circles), adenomas (n=73, solid squares), Stage 1 (n=12, open squares), Stage R (n=21, open circles), Stage III (n=23, open diamonds) and Stage IV (n=12, black crosses). The signal output was converted to a mass using a calibration curve. Data is given as pg methylated CAHM per mL plasma. Data are mean values of triplicate. Increased masses of methylated CAHM was observed in blood plasma from patients as a function of disease progression (i.e. pg/mL CAHM was calculated to be higher in Stage II-IV compared Stage I-H). In contrast, high and similar levels of pg methylated CAHM was measured in colorectal tissue from the earliest onset of disease (precancerous) to late stage cancer. C: The levels of methylated CAHM was measured and plotted in a scatter graph of pg methylated CAHM/ml plasma (log 10) vs. wt DNA ng/mL plasma from colonoscopy-confirmed patients including normals (n=74, solid circles), adenomas (n=73, solid squares), Stage I (n=12, open squares), Stage II (n=21, open circles), Stage I (n=23, open diamonds) and Stage IV (n=12, black crosses).
Figure 2:
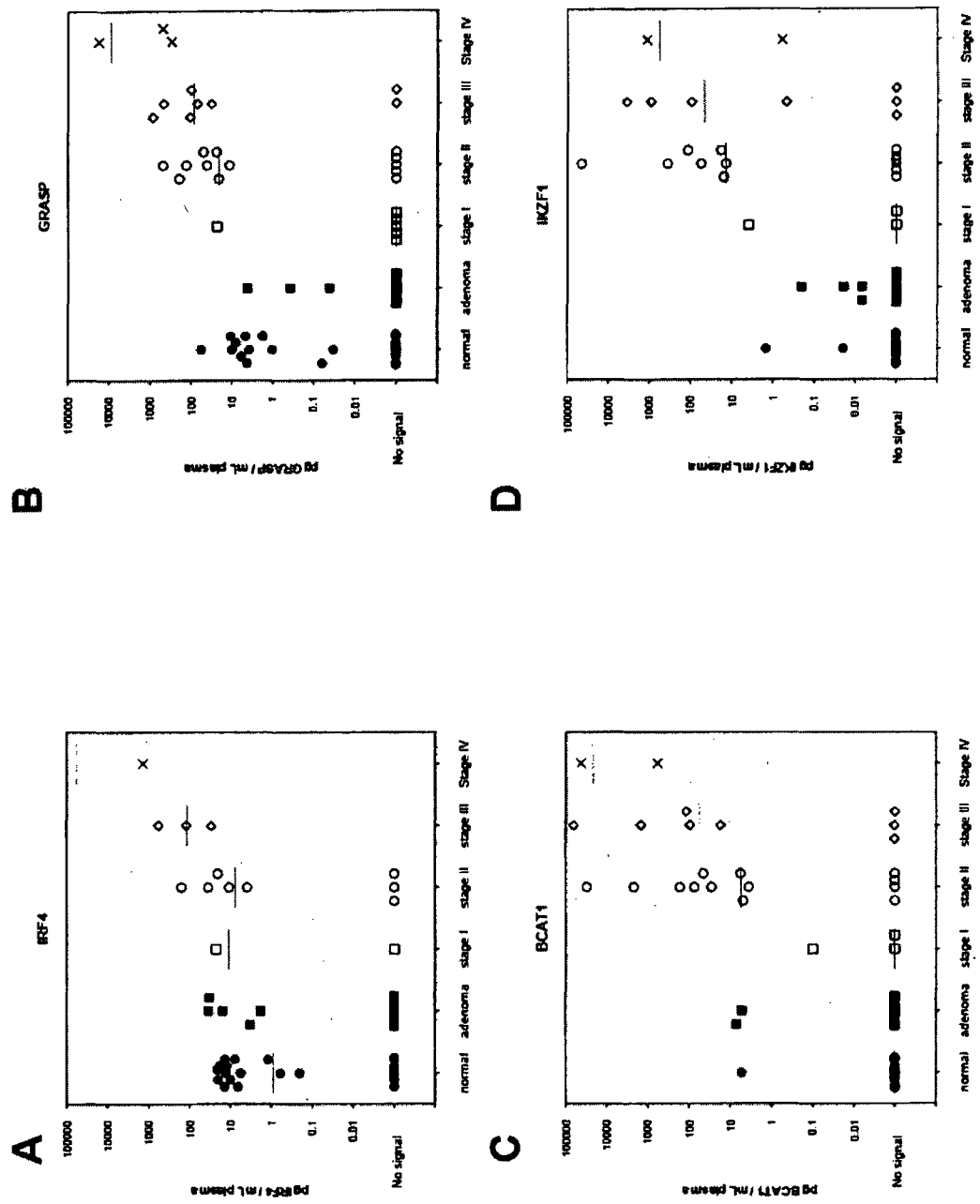
FIG. 2. Increased levels of methylated colorectal cancer biomarkers in blood plasma as a function of disease progression. Measurement of CAHM methylation levels in tissue and blood plasma specimens. The levels of methylated IRF4 (A), GRASP (B), BCAT1 (C) and IKZF1 (D) were measured in the equivalent of triplicate analysis of 0.5 mL plasma from colonoscopy-confirmed patients including normals (solid circles), adenomas (solid squares), Stage I (open squares), Stage II (open circles), Stage III (open diamonds) and Stage IV (crosses). The signal output was converted to a mass/well using a calibration curve. Data is given as pg methylated biomarker per mL plasma. Data are mean values of triplicate. As exemplified in FIG. 1 for CAHM, FIG. 2 demonstrates another four biomarkers, namely, GRASP, IRF4, BCAT1 and IKZF1, where measurement of blood plasma methylation levels may be indicative of colorectal cancer progression.

The present invention is predicated, in part, on the determination that several genes which are known to exhibit increased levels of methylation in individuals exhibiting large intestine neoplasms are also an indicator of the classification of the neoplasm. Specifically, it has been surprisingly determined that although the relative increase in DNA methylation levels of a given gene marker is relatively consistent in a tissue biopsy irrespective of the stage or grade of the neoplasm in issue, the same is not true if a blood-derived sample, such as plasma, is analysed. In particular, whereas a blood-derived sample will also show increased levels of DNA methylation in the context of the presence of a large intestine malignancy, these increased methylation levels become progressively more increased as the malignancy becomes more advanced. This is not observed in tissue specimens. Accordingly, by assessing DNA methylation levels in accordance with the method of the present invention, one can determine not only whether or not malignant transformation has occurred, but further the likely probability that the malignancy would be classified as early stage or late stage.

Accordingly, one aspect of the present invention is directed to a method of determining one or more probabilities of respective classifications of a large intestine neoplasm in an individual, said method comprising assessing the methylation status of a DNA region selected from:
(i) the region, including 2 kb upstream of the transcription start site, defined by at least one of Hg19 coordinates:
  (1) chr12:24962958 . . . 25102393
  (2) chr7:50344378 . . . 50472798
  (3) chr6:391739 . . . 411443;
  (4) chr12:52400748 . . . 52409671; and
  (5) chr6:163834097 . . . 163834982; or
(ii) the gene region, including 2 kb upstream of at least one of:

| | | | | |
|---|---|---|---|---|
| (1) BCAT1 | (2) IKZF1 | (3) IRF4 | (4) GRASP and | (5) CAHM | in a blood-derived sample from said individual, wherein a level of methylation of at least one of the DNA regions of group (i) and/or (ii) relative to corresponding measured levels of methylation from a population of individuals with known neoplastic categories of corresponding large intestine neoplasms is used to determine one or more probabilities of respective classifications of said large intestine neoplasm of said individual into one or more neoplastic categories selected from adenoma, stage I, stage II, stage III, and stage IV categories or into one or more aggregates of fewer than five of said neoplastic categories.

In one embodiment, the method is directed to determining one or more probabilities of respective classifications of said large intestine neoplasms of said individual into one or more aggregates of fewer than five of said neoplastic categories.

The method may further include using said level of methylation for said individual to determine a probability that said large intestine of said individual would be classified as non-neoplastic, based on comparison of said level of methylation relative to said corresponding measured levels of methylation and to further corresponding measured levels of methylation from a further population of individuals whose large intestines were classified as non-neoplastic.

The aggregate categories may include one or more aggregates of fewer than five of said neoplastic categories and an aggregate of the non-neoplastic category with at least the adenoma category.

The aggregate categories may include a pre-malignant neoplasm category consisting of an aggregate of the non-neoplastic and adenoma categories.

The aggregate categories may include an early stage malignant neoplasm category consisting of an aggregate of the stage I and stage II categories.

The aggregate categories may include a late stage malignant neoplasm category consisting of an aggregate of the stage III and stage IV categories.

The aggregate categories may include the pre-malignant neoplasm category, early stage malignant neoplasm category, and late stage malignant neoplasm categories.

Given measured levels of methylation in a population of individuals with known classifications of large intestine neoplasms into neoplastic categories selected from adenoma, stage I, stage II, stage III, and stage IV categories or aggregates of fewer than five of said neoplastic categories, and further measured levels of methylation in a further population of individuals whose large intestines were classified as non-neoplastic, the prior statistical relationships between the measured methylation levels and the corresponding known categories for the populations of individuals can be used to determine one or more probabilities that a further measured methylation level of an individual corresponds to respective ones of the same categories of the large intestine neoplasm or non-neoplastic large intestine of said individual. As will be apparent to those skilled in the art, the determination can be made using any one of a variety of standard statistical methods, including Bayesian statistics and machine learning.

In some embodiments, the statistical method includes generating histograms wherein the measured levels of methylation corresponding to known categories are allocated into bins of respective ranges of methylation levels and using these histograms to estimate at least one probability that a further measured methylation level corresponds to at least one of the known categories. As will be apparent to those skilled in the art, there are many methods to estimate classification probabilities. For example, by adding the total sizes of the bins corresponding to methylation levels of equal or lesser levels to the methylation level in question and dividing this sum by the total across all bins, one can estimate the proportion of methylation levels at or below a given level which are of a known category and thus the probability that a measured methylation level is of said category.

In some embodiments, the statistical distributions of said measured levels of methylation are modelled by standard statistical distributions such as a Gaussian distribution, for example, and a standard fitting or regression procedure such as maximum likelihood is used to determine the parameters of the distributions, which can then be applied to a further measured level of methylation from an individual to determine one or more probabilities that the large intestine of that individual would be classified as respective ones of the neoplastic categories and the non-neoplastic category.

In some embodiments, the method may include using the determined probabilities to automatically classify the large intestine neoplasm of the individual into one of the prior known classifications, whether neoplastic or non-neoplastic. However, given the overlap between measured levels of methylation for the different categories, the probabilities are generally more useful for the selection of possible further medical treatment options.

In other embodiments, the statistical associations between the measured methylation levels on the one hand and the corresponding categories observed by colonoscopy or surgery on the other are used as a training set for supervised learning. The resulting weights are then applied to at least one further measured methylation level for at least one further individual in order to determine corresponding probabilities for membership of those categories for that at least one individual. As will be apparent to those skilled in the art, any one of a number of standard supervised training methods can be used.

The categories used for supervised learning may include all five neoplastic categories and the non-neoplastic category, or aggregates of those six categories, such as the aggregate categories described above. The selection of which categories to use for supervised training may be based on diagnostic/treatment requirements and/or the available number and/or classification confidence of the observed categories (e.g., in order to improve sensitivity and specificity of classification). In any case, the weights generated by supervised learning can also be provided as inputs to a standard classifier in order to classify the large intestine of the individual into a neoplastic or non-neoplastic class or category based on the corresponding measured methylation level.

Reference to "neoplasm" should be understood as a reference to a lesion, tumour or other encapsulated or unencapsulated mass or other form of growth which comprises neoplastic cells. A 'neoplastic cell' should be understood as a reference to a cell exhibiting abnormal growth. The term "growth" should be understood in its broadest sense and includes reference to proliferation. In this regard, an example of abnormal cell growth is the uncontrolled proliferation of a cell. Another example is failed apoptosis in a cell, thus prolonging its usual life span. The neoplastic cell may be a benign cell or a malignant cell. In a preferred embodiment, the subject neoplasm is an adenoma or an adenocarcinoma. Without limiting the present invention to any one theory or mode of action, an adenoma is generally a benign tumour of epithelial origin which is either derived from epithelial tissue or exhibits clearly defined epithelial structures. These structures may take on a glandular appearance. It can comprise a malignant cell population within the adenoma, such as occurs with the progression of a benign adenoma or benign neoplastic legion to a malignant adenocarcinoma.

Reference to "large intestine" should be understood as a reference to a cell derived from one of the eight anatomical regions of the large intestine, which regions commence after the terminal region of the ileum, these being:
  (i) the cecum;
  (ii) the ascending colon;
  (iii) the transverse colon;
  (iv) the descending colon;
  (v) the sigmoid colon;
  (vi) the rectum;
  (vii) the splenic flexure; and
  (viii) the hepatic flexure.

Preferably, said neoplastic cell is an adenoma or adenocarcinoma and even more preferably a colorectal adenoma or adenocarcinoma.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. As detailed hereinbefore, the chromosomal coordinates correspond to the Hg19 version of the genome. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

It should be understood that the "individual" who is the subject of testing may be any human or non-human mammal. Examples of non-human mammals includes primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. deer, foxes).

Preferably, said mammal is a human.

As detailed hereinbefore, the method of the present invention enables one to assess the probability that a neoplasm is a premalignant neoplasm, early stage malignancy or late stage malignancy. Although the staging and grading systems which are commonly used by pathologists in the context of large intestine neoplasms (such as colorectal cancers) can purportedly stage such cancers quite precisely, the fact is that they require a biopsy specimen to be harvested, this being a procedure which is invasive. Since the assessment required to be performed is the preparation and histological analysis of a tissue section, it can also take some time to obtain results. In terms of accurately assessing histological specimens, the interpretation of the sections is subjective and can be extremely difficult and unreliable, particularly in the context of moderate grade cancers, as opposed to very early stage cancers or metastatic cancers. Accordingly, the identification of a molecular basis upon which to classify a neoplasm is a significant advance due to the fact that such analyses are not subjective. Still further, since the DNA methylation levels of the genes at issue are assessed in a blood sample, this is the first available non-invasive means of classifying a large intestine neoplasm.

Without limiting the present invention to any one theory or mode of action, the most commonly used staging system for colorectal cancer is that of the American Joint Committee on Cancer (AJCC), sometimes also known as the TNM system. The TNM system describes 3 key pieces of information:
  T describes how, far the main (primary) tumour has grown into the wall of the intestine and whether it has grown into nearby areas.
  N describes the extent of spread to nearby (regional) lymph nodes.
  M indicates whether the cancer has metastasized.

Numbers or letters appear after T, N, and M to provide more details about each of these factors. The numbers 0 through 4 indicate increasing severity.

A detailed description in relation to how the TNM system is applied has been detailed earlier.

Once a person's T, N, and M categories have been determined, usually after surgery, this information is combined in a process called stage grouping. The stage is expressed in Roman numerals from stage I (the least advanced) to stage IV (the most advanced). Nevertheless, despite the apparent theoretical precision with which staging parameters are classified, the reality in terms of assessing these parameters is far less precise. The present method has enabled a simpler and more reliable staging system to be made available. Specifically, a patient is assessed to determine the probability that a neoplasm is a "premalignant neoplasm", "early stage malignant neoplasm" or "late stage malignant neoplasm". Based on these results, one may elect to also have a biopsy or some other diagnostic procedure performed. Alternatively one may use these results to inform what therapeutic or palliative care regime should be designed and implemented. Of particular advantage is the fact that this method enables ongoing testing to be performed. This may be particularly relevant where a premalignant neoplasm has been identified and a decision has been made not to surgically remove the neoplasm in the first instance but to attempt to treat it.

In the context of the present invention, reference to "premalignant neoplasm" should be understood as a reference to a neoplasm which is not malignant. An example of a non-malignant neoplasm is an adenoma. Without limiting the present invention in any way, the histological and functional characteristics of a premalignant large intestine neoplasm are evidence of new, abnormal tissue growth without evidence of invasion.

Reference to an "early stage malignant neoplasm" is a reference to a large intestine neoplasm which has become malignant but which is unlikely to extend beyond the bowel wall.

Reference to a "late stage malignant neoplasm" should be understood as a reference to a large intestine neoplasm which is malignant and which has spread to lymph nodes or distant organs. Reference to late stage malignant neoplasms includes, for example, neoplasms which have become metastatic.

In terms of screening for the methylation of these gene regions, it should be understood that the assays can be designed to screen either the specific regions listed herein (which correspond to the "plus" strand of the gene) or the complementary "minus" strand. It is well within the skill of the person in the art to choose which strand to analyse and to target that strand based on the chromosomal coordinates provided herein. In some circumstances, assays may be established to screen both strands.

Without limiting the present invention to any one theory or mode of action, although measuring the methylation levels across these DNA regions is diagnostic of the classification of a large intestine neoplastic condition, it has been determined that discrete subregions are particularly useful in this regard since these subregions contain a high density of CpG dinucleotides which are frequently hypermethylated in large intestine neoplasias, such as colorectal cancers. This finding renders these subregions a particularly useful target for analysis since it both simplifies the screening process due to a shorter more clearly defined region of DNA requiring analysis and, further, the fact that the results from these regions will provide a significantly more definitive result in relation to the presence, or not, of hypermethylation than would be obtained if analysis was performed across the DNA region as a whole. This finding therefore both simplifies the screening process and increases the sensitivity of large intestine neoplasia diagnosis.

The subregions which have been determined to exhibit particular utility are listed below with reference to the gene and chromosomal region within which they are found:
(1) BCAT1 subregions chr12:25101992-25102093 (SEQ ID NO:1 or the corresponding minus strand) and chr12: 25101909-25101995 (SEQ ID NO:2 or the corresponding minus strand)
(2) IKZF1 subregions: chr7:50343867-50343961 (SEQ ID NO:3 or the corresponding minus strand) and chr7: 50343804-5033895 (SEQ ID NO:4 or the corresponding minus strand)
(3) IRF4 subregions chr6:392036-392145 (SEQ ID NO:5 or the corresponding minus strand)
(4) GRASP subregions: chr12:52399672-52399922, chr12: 52400821-52401051 (SEQ ID NO:6 or the corresponding minus strand), chr12:52401407-52401664 (SEQ ID NO:7 or the corresponding minus strand) chr12:52400866-52400973 and Chr12:52401107-52401664.
(5) CAHM subregions: chr6:163834295-163834500 (SEQ ID NO:8), chr6:163834621-163834906, chr6:163834393-163834455 and chr6:163834393-163834519.

Without limiting the present invention to any one theory or mode of action, the skilled person may screen one or more subregions for each gene marker.

Without limiting the present invention to any one theory or mode of action, DNA methylation is universal in bacteria, plants, and animals. DNA methylation is a type of chemical modification of DNA that is stable over rounds of cell division but does not involve changes in the underlying DNA sequence of the organism. Chromatin and DNA modifications are two important features of epigenetics and play a role in the process of cellular differentiation; allowing cells to stably maintain different characteristics despite containing the same genomic material. In eukaryotic organisms DNA methylation occurs only at the number 5 carbon of the cytosine pyrimidine ring. In mammals, DNA methylation occurs mostly at the number 5 carbon of the cytosine of a CpG dinucleotide. CpG dinucleotides comprise approximately 1% human genome.

70-80% of all CpGs are methylated. CpGs may be grouped in clusters called "CpG islands" that are present in the 5' regulatory regions of many genes and are frequently unmethylated. In many disease processes such as cancer, gene promoters and/or CpG islands acquire abnormal hypermethylation, which is associated with heritable transcriptional silencing. DNA methylation may impact the transcription of genes in two ways. First, the methylation of DNA may itself physically impede the binding of transcriptional proteins to the gene, thus blocking transcription. Second, methylated DNA may be bound by proteins known as Methyl-CpG-binding domain proteins (MBDs). MBD proteins then recruit additional proteins to the locus, such as histone deacetylases and other chromatin remodelling proteins that can modify histones, thereby forming compact, inactive chromatin termed silent chromatin. This link between DNA methylation and chromatin structure is very important. In particular, loss of Methyl-CpG-binding Protein 2 (MeCP2) has been implicated in Rett syndrome and Methyl-CpG binding domain protein 2 (MBD2) mediates the transcriptional silencing of hypermethylated genes in cancer.

In humans, the process of DNA methylation is carried out by three enzymes, DNA methyltransferase 1, 3a and 3b (DNMT1, DNMT3a, DNMT3b). It is thought that DNMT3a and DNMT3b are the de novo methyltransferases that set up DNA methylation patterns early in development. DNMT1 is the proposed maintenance methyltransferase that is responsible for copying. DNA methylation patterns to the daughter strands during DNA replication. DNMT3L is a protein that is homologous to the other DNMT3s but has no catalytic activity. Instead, DNMT3L assists the de novo methyltransferases by increasing their ability to bind to DNA and stimulating their activity. Finally, DNMT2 has been identified as an "enigmatic" DNA methylstransferase homolog, containing all 10 sequence motifs common to all DNA methyltransferases; however, DNMT2 may not methylate DNA but instead has been shown to methylate a small RNA.

"Methylation status" should therefore be understood as a reference to the presence, absence and/or quantity of methylation at a particular nucleotide, or nucleotides, within a DNA region. The methylation status of a particular DNA sequence (e.g. DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of the methylation status. This is of particular use when it is desirable to compare the methylation status of a sequence in a sample to a threshold value.

The term "methylation" shall be taken to mean the presence of a methyl group added by the action of a DNA methyl transferase enzyme to a cytosine base or bases in a region of nucleic acid, e.g. genomic DNA. As described herein, there are several methods known to those skilled in the art for determining the level or degree of methylation of nucleic acid.

By "higher level" is meant that there are a higher number of methylated CpG dinucleotides in the subject diagnosed than in a control sample, that is, either the proportion of DNA molecules methylated at a particular CpG site is higher or there are a higher number of separate CpG sites methylated in the subject. It should be understood that the terms "enhanced" and "increased" are used interchangeably with the term "higher".

The present invention is not to be limited by a precise number of methylated residues that are considered to be diagnostic of neoplasia in a subject, because some variation between patient samples will occur. The present invention is also not limited by positioning of the methylated residue.

Nevertheless, a number of specific cytosine residues which undergo hypermethylation within these subregions have also been identified. In another embodiment, therefore, a screening method can be employed which is specifically directed to assessing the methylation status of one or more of either these residues or the corresponding cytosine at position n+1 on the opposite DNA strand.

To this end, detailed in Table 2 are the cytosine residues which have been identified in this regard. It should be appreciated by the person of skill in the art that these individual residues are numbered by reference to Hg19, which also corresponds to the numbering of the specific subregions listed hereinbefore and which can be further identified when the coordinate numbering for each subregion is applied to the corresponding subregion sequences which are provided in the sequence listing. It should be understood that these residues have been identified in the context of the subregion DNA. However, there are other residues which are hypermethylated outside the subregions themselves but within the larger DNA region from which the subregions derive. Accordingly, these specified residues represent a particularly useful subset of individual cytosine residues which undergo hypermethylation within the context of the DNA regions and subregions herein disclosed. These individual residues are grouped below according to the DNA region within which they occur. These DNA regions are identified by reference to both the Hg19 chromosomal coordinates and the gene region name.

To the extent that the method of the present invention includes analysing the methylation of BCAT1, the subject residues:

| | | |
|---|---|---|
| chr12:25101998 | chr12:25102003 | chr12:25102006 |
| chr12:25102009 | chr12:25102017 | chr12:25102022 |
| chr12:25102039 | chr12:25102048 | chr12:25102050 |
| chr12:25102053 | chr12:25102061 | chr12:25102063 |
| chr12:25102071 | chr12:25101921 | chr12:25101934 |
| chr12:25101943 | chr12:25101951 | chr12:25101962 |
| chr12:25101964 | chr12:25101970 | | or a corresponding cytosine at position n+1 on the opposite DNA strand.

To the extent that the method of the present invention includes analysing the methylation of GRASP, the subject residues are:

| | | |
|---|---|---|
| chr12:52399713 | chr12:52399731 | chr12:52399749 |
| chr12:52399783 | chr12:52399796 | chr12:52399808 |
| chr12:52399823 | chr12:52399835 | chr12:52399891 |
| chr12:52400847 | chr12:52400850 | chr12:52400859 |
| chr12:52400866 | chr12:52400869 | chr12:52400873 |
| chr12:52400881 | chr12:52400886 | chr12:52400893 |
| chr12:52400895 | chr12:52400899 | chr12:52400902 |
| chr12:52400907 | chr12:52400913 | chr12:52400919 |
| chr12:52400932 | chr12:52400938 | chr12:52400958 |
| chr12:52400962 | chr12:52400971 | chr12:52400973 |
| chr12:52400976 | chr12:52400998 | chr12:52401008 |
| chr12:52401010 | chr12:52401012 | chr12:52401016 |
| chr12:52401019 | chr12:52401025 | chr12:52401041 |
| chr12:52401044 | chr12:52401053 | chr12:52401060 |
| chr12:52401064 | chr12:52401092 | chr12:52401118 |
| chr12:52401438 | chr12:52401448 | chr12:52401460 |
| chr12:52401465 | chr12:52401474 | chr12:52401477 |
| chr12:52401479 | chr12:52401483 | chr12:52401504 |
| chr12:52401514 | chr12:52401523 | chr12:52401540 |
| chr12:52401553 | chr12:52401576 | chr12:52401588 |
| chr12:52401595 | chr12:52401599 | chr12:52401604 |
| chr12:52401606 | chr12:52401634 | chr12:52401640 |
| chr12:52401644 | chr12:52401659 | chr12:52401160 |
| chr12:52401165 | chr12:52401174 | chr12:52401177 |
| chr12:52401179 | chr12:52401183 | chr12:52401204 |
| chr12:52401215 | chr12:52401223 | chr12:52401240 |
| chr12:52401253 | chr12:52401288 | chr12:52401295 |
| chr12:52401299 | chr12:52401304 | chr12:52401334 |
| chr12:52401340 | chr12:52401344 | chr12:52401359 | or a corresponding cytosine at position n+1 on the opposite DNA strand.

To the extent that the method of the present invention includes analysing the methylation of CAHM, the subject residues are:

| | | |
|---|---|---|
| chr6:163834330 | chr6:163834332 | chr6:163834357 |
| chr6:163834373 | chr6:163834384 | chr6:163834390 |
| chr6:163834392 | chr6:163834406 | chr6:163834412 |
| chr6:163834419 | chr6:163834443 | chr6:163834448 |
| chr6:163834452 | chr6:163834464 | chr6:163834483 |
| chr6:163834653 | chr6:163834660 | chr6:163834672 |
| chr6:163834675 | chr6:163834678 | chr6:163834681 |
| chr6:163834815 | chr6:163834824 | chr6:163834835 |
| chr6:163834840 | chr6:163834853 | chr6:163834855 |
| chr6:163834858 | chr6:163834863 | chr6:163834869 |
| chr6:163834872 | | | or a corresponding cytosine at position n+1 on the opposite DNA strand.

To the extent that the method of the present invention includes analysing the methylation of IKZF1, the subject residues are:

| | | |
|---|---|---|
| chr7:50343869 | chr7:50343872 | chr7:50343883 |
| chr7:50343889 | chr7:50343890 | chr7:50343897 |
| chr7:50343907 | chr7:50343909 | chr7:50343914 |
| chr7:50343934 | chr7:50343939 | chr7:50343950 |
| chr7:50343959 | chr7:50343805 | chr7:50343822 |
| chr7:50343824 | chr7:50343826 | chr7:50343829 |
| chr7:50343831 | chr7:50343833 | chr7:50343838 |
| chr7:50343847 | chr7:50343850 | chr7:50343858 |
| chr7:50343864 | chr7:50343869 | chr7:50343872 |
| chr7:50343890 | | | or a corresponding cytosine at position n+1 on the opposite DNA strand.

To the extent that the method of the present invention includes analysing the methylation of IRF4, the subject residues are:

| | | |
|---|---|---|
| chr6:392036 | chr6:392047 | chr6:392049 |
| chr6:392057 | chr6:392060 | chr6:392066 |
| chr6:392080 | chr6:392094 | chr6:392102 |
| chr6:392131 | | | or a corresponding cytosine at position n+1 on the opposite DNA strand.

The detection method of the present invention can be performed on any suitable blood sample. To this end, reference to a "blood sample" should be understood as a reference to any sample deriving from blood such as, but not limited to, whole blood, serum or plasma. The blood sample which is tested according to the method of the present invention may be tested directly or may require some form of treatment prior to testing. For example, it may require permeabilisation prior to testing. In one embodiment, the blood sample is a plasma sample.

To the extent that the DNA region of interest is present in a biological sample, the biological sample may be directly tested or else all or some of the nucleic acid present in the biological sample may be isolated prior to testing. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target cell population or molecules derived therefrom to be treated prior to testing, for example, inactivation of live virus. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation.

Although the present method is directed to classifying a large intestine neoplasm, the method of the invention is also useful as a means to monitor disease progression. This can be important in situations such as where a decision has been made not to excise an early stage tumour or, even where surgery has been performed on the primary tumour, to monitor for the development of metastases which may not have been visually detectable at the time that the primary tumor was identified. One may also seek to monitor a patient during a treatment regime for a premalignant or early stage malignancy in order to detect likely transition to a higher stage malignancy.

The method of the invention can be used to evaluate individuals known or suspected to have a neoplasia or as a routine clinical test, i.e., in an individual not necessarily suspected to have a neoplasia.

Further, the present methods may be used to assess the efficacy of a course of treatment. For example, the efficacy of an anti-cancer treatment can be assessed by monitoring DNA methylation of the sequences described herein over time in a mammal having cancer.

The method of the present invention is therefore useful as a one-time test or as an ongoing monitor of those individuals thought to be at risk of neoplasia development or as a monitor of the effectiveness of therapeutic or prophylactic treatment regimes directed to inhibiting or otherwise slowing neoplasia development. In these situations, mapping the modulation of methylation levels in any one or more classes of biological samples is a valuable indicator of the status of an individual or the effectiveness of a therapeutic or prophylactic regime which is currently in use.

Any method for detecting DNA methylation can be used in the methods of the present invention. A number of methods are available for detection of differentially methylated DNA at specific loci in either primary tissue samples or in patient samples such as blood, urine, stool or saliva (reviewed in Kristensen and Hansen *Clin Chem.* 55:1471-83, 2009; Ammerpohl et al. *Biochim Biophys Acta.* 1790:847-62, 2009; Shames et al. *Cancer Lett.* 251:187-98, 2007; Clark et al. *Nat Protoc.* 1:2353-64, 2006). For analysis of the proportion or extent of DNA methylation in a target gene, DNA is normally treated with sodium bisulfite and regions of interest amplified using primers and PCR conditions that will amplify independently of the methylation status of the DNA. The methylation of the overall amplicon or individual CpG sites can then be assessed by sequencing, including pyrosequencing, restriction enzyme digestion (COBRA) or by melting curve analysis. Alternatively ligation-based methods for analysis of methylation at specific CpG sites may be used. Detection of aberrantly methylated DNA released from tumours and into bodily fluids is being developed as a means of cancer diagnosis. Here, in the case of hypermethylated sequences, it is necessary to use sensitive methods that allow the selective amplification of the methylated DNA sequence from a background of normal cellular DNA that is unmethylated. Such methods based on bisulfite-treated DNA, for example; include methylation selective PCR (MSP), Heavymethyl PCR, Headloop PCR and Helper-dependent chain reaction (PCT/AU2008/001475).

Briefly, in some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copieand comparing the quantity to a control, average methylation density of a locus can be determined. A methylation-sensitive enzyme is one which cuts DNA if its recognition sequence is unmethylated while a methylation-dependent enzyme cuts DNA if its recognition sequence is methylated. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

Kits for the above methods can include, e.g., one or more of methylation-dependent restriction enzymes, methylation-sensitive restriction enzymes, amplification (e.g., PCR) reagents, probes and/or primers.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2):163-79 (2002). Amplifications may be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated verses unmethylated DNA. See, Herman et al. *Proc. Natl. Acad. Sci. USA* 93:9821-9826 (1996); U.S. Pat. No. 5,786,146.

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of methylated DNA, (or alternatively to unmethylated sequences) amplification can indicate methylation status of sequences where the primers hybridize. Furthermore, the amplification product can be detected with a probe that specifically binds to a sequence resulting from bisulfite treatment of an unmethylated DNA. If desired, both primers and probes can be used to detect methylation status. Thus, kits for use with MethyLight can include sodium bisulfite as well as primers or detectably-labelled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labelled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Additional methylation detection methods include, but are not limited to, methylated CpG island amplification (see, Toyota et al.: *Cancer Res.* 59:2307-12 (1999)) and those described in, e.g., U.S. Patent Publication 2005/0069879; Rein, et al. *Nucleic Acids Res.* 26 (10): 2255-64 (1998); Olek, et al. *Nat. Genet.* 17(3): 275-6 (1997); and PCT Publication No. WO 00/70090.

More detailed information in relation to several of these generally described methods is provided below:

(a) Probe or Primer Design and/or Production

Several methods described herein for the diagnosis of a neoplasia use one or more probes and/or primers. Methods for designing probes and/or primers for use in, for example, PCR or hybridization are known in the art and described, for example, in Dieffenbach and Dveksler (Eds) (In: PCR Primer: A Laboratory Manual, Cold Spring Harbor Laboratories, NY, 1995). Furthermore, several software packages are publicly available that design optimal probes and/or primers for a variety of assays, e.g. Primer 3 available from the Center for Genome Research, Cambridge, Mass., USA.

Clearly, the potential use of the probe or primer should be considered during its design. For example, should the probe or primer be produced for use in a methylation specific PCR or ligase chain reaction (LCR) assay the nucleotide at the 3' end (or 5' end in the case of LCR) should preferably correspond to a methylated nucleotide in a nucleic acid.

Probes and/or primers useful for detection of a sequence associated with a neoplasia are assessed, for example, to determine those that do not form hairpins, self-prime or form primer dimers (e.g. with another probe or primer used in a detection assay). Furthermore, a probe or primer (or the sequence thereof) is often assessed to determine the temperature at which it denatures from a target nucleic acid (i.e. the melting temperature of the probe or primer, or Tm). Methods for estimating Tm are known in the art and described, for example, in Santa Lucia, *Proc. Natl. Acad. Sci. USA*, 95: 1460-1465, 1995 or Bresslauer et al., *Proc. Natl. Acad. Sci. USA*, 83: 3746-3750, 1986.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by Messing, *Methods Enzymol*, 101, 20-78, 1983. Other methods for oligonucleotide synthesis include, for example, phosphotriester and phosphodiester methods (Narang, et al. *Meth. Enzymol* 68: 90, 1979) and synthesis on a support (Beaucage, et al. *Tetrahedron Letters* 22:1859-1862, 1981) as well as phosphoramidate technique, Caruthers, M. H., et al., *Methods in Enzymology*, Vol. 154, pp. 287-314 (1988), and others described in "Synthesis and Applications of DNA and RNA," S. A. Narang, editor, Academic Press, New York, 1987, and the references cited therein. Probes comprising locked nucleic acid (LNA) are synthesized as described, for example, in Nielsen et al. *J. Chem. Soc. Perkin Trans.*, 1:3423, 1997; Singh and Wengel, *Chem. Commun.* 1247, 1998. While, probes comprising peptide-nucleic acid (PNA) are synthesized as described, for example, in Egholm et al., *Am. Chem. Soc.*, 114:1895, 1992; Egholm et al., *Nature*, 365:566, 1993; and Orum et al., *Nucl. Acids Res*, 21:5332, 1993.

(b) Methylation-Sensitive Endonuclease Digestion of DNA

In one example, the increased methylation in a sample is determined using a process comprising treating the nucleic acid with an amount of a methylation-sensitive restriction endonuclease enzyme under conditions sufficient for nucleic acid to be digested and then detecting the fragments produced. Exemplary methylation-sensitive endonucleases include, for example, HhaI or HpaII. Preferably, assays include internal controls that are digested with a methylation-insensitive enzyme having the same specificity as the methylation-sensitive enzyme employed. For example, the methylation-insensitive enzyme MspI is an isoschizomer of the methylation-sensitive enzyme HpaII.

Hybridization Assay Formats

In one example, the digestion of nucleic acid is detected by selective hybridization of a probe or primer to the undigested nucleic acid. Alternatively, the probe selectively hybridizes to both digested and undigested nucleic acid but facilitates differentiation between both forms, e.g., by electrophoresis. Suitable detection methods for achieving selective hybridization to a hybridization probe include, for example, Southern or other nucleic acid hybridization (Kawai et al., *Mol. Cell. Biol.* 14:7421-7427, 1994; Gonzalgo et al., *Cancer Res.* 57:594-599, 1997).

Suitable hybridization conditions are determined based on the melting temperature (Tm) of a nucleic acid duplex comprising the probe. The skilled artisan will be aware that optimum hybridization reaction conditions should be determined empirically for each probe, although some generalities can be applied. Preferably, hybridizations employing short oligonucleotide probes are performed at low to medium stringency. In the case of a GC rich probe or primer or a longer probe or primer a high stringency hybridization and/or wash is preferred. A high stringency is defined herein as being a hybridization and/or wash carried out in about 0.1×SSC buffer and/or about 0.1% (w/v) SDS, or lower salt concentration, and/or at a temperature of at least 65° C., or equivalent conditions. Reference herein to a particular level of stringency encompasses equivalent conditions using wash/hybridization solutions other than SSC known to those skilled in the art.

In accordance with the present example, a difference in the fragments produced for the test sample and a negative control sample is indicative of the subject having a neoplasia. Similarly, in cases where the control sample comprises data from a tumor, cancer tissue or a cancerous cell or pre-cancerous cell, similarity, albeit not necessarily absolute identity, between the test sample and the control sample is indicative of a positive diagnosis (i.e. cancer).

Amplification Assay Formats

In an alternative example, the fragments produced by the restriction enzyme are detected using an amplification system, such as, for example, polymerase chain reaction (PCR), rolling circle amplification (RCA), inverse polymerase chain reaction (iPCR), in situ PCR (Singer-Sam et al., *Nucl. Acids Res.* 18:687, 1990), strand displacement amplification (SDA) or cycling probe technology.

Methods of PCR are known in the art and described, for example, by McPherson et al., PCR: A Practical Approach. (series eds, D. Rickwood and B. D. Hames), IRL Press Limited, Oxford. pp 1-253, 1991 and by Dieffenbach (ed) and Dveksler (ed) (In: PCR Primer: A Laboratory Manual, Cold Spring Harbour Laboratories, NY, 1995), the contents of which are each incorporated in their entirety by way of reference. Generally, for PCR two non-complementary nucleic acid primer molecules comprising at least about 18 nucleotides in length, and more preferably at least 20-30 nucleotides in length are hybridized to different strands of a nucleic acid template molecule at their respective annealing sites, and specific nucleic acid molecule copies of the template that intervene the annealing sites are amplified enzymatically. Amplification products may be detected, for example, using electrophoresis and detection with a detectable marker that binds nucleic acids. Alternatively, one or more of the oligonucleotides are labelled with a detectable marker (e.g. a fluorophore) and the amplification product detected using, for example, a lightcycler (Perkin Elmer, Wellesley, Mass., USA, Roche Applied Science, Indianapolis, Ind., USA).

Strand displacement amplification (SDA) utilizes oligonucleotide primers, a DNA polymerase and a restriction endonuclease to amplify a target sequence. The oligonucleotides are hybridized to a target nucleic acid and the polymerase is used to produce a copy of the region intervening the primer annealing sites. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Cycling Probe Technology uses a chimeric synthetic primer that comprises DNA-RNA-DNA that is capable of hybridizing to a target sequence. Upon hybridization to a target sequence the RNA-DNA duplex formed is a target for RNaseH thereby cleaving the primer. The cleaved primer is then detected, for example, using mass spectrometry or electrophoresis.

For primers that flank or are adjacent to a methylation-sensitive endonuclease recognition site, it is preferred that such primers flank only those sites that are hypermethylated in neoplasia to ensure that a diagnostic amplification product is produced. In this regard, an amplification product will only be produced when the restriction site is not cleaved, i.e., when it is methylated. Accordingly, detection of an amplification product indicates that the CpG dinucleotide/s of interest is/are methylated.

As will be known to the skilled artisan, the precise length of the amplified product will vary depending upon the distance between the primers. Clearly this form of analysis may be used to determine the methylation status of a plurality of CpG dinucleotides provided that each dinucleotide is within a methylation sensitive restriction endonuclease site. In these methods, one or more of the primers may be labelled with a detectable marker to facilitate rapid detection of amplified nucleic acid, for example, a fluorescent label (e.g. Cy5 or Cy3) or a radioisotope (e.g. $^{32}P$).

The amplified nucleic acids are generally analyzed using, for example, non-denaturing agarose gel electrophoresis, non-denaturing polyacrylamide gel electrophoresis, mass spectrometry, liquid chromatography (e.g. HPLC or dHPLC), or capillary electrophoresis. (e.g. MALDI-TOF). High throughput detection methods, such as, for example, matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or DNA chip technology (e.g., WO98/49557; WO 96/17958; Fodor et al., Science 767-773, 1991; U.S. Pat. Nos. 5,143,854; and 5,837,832, the contents of which are all incorporated herein by reference), are especially preferred for all assay formats described herein. Alternatively, amplification of a nucleic acid may be continuously monitored using a melting curve analysis method as described herein and/or in, for example, U.S. Pat. No. 6,174,670, which is incorporated herein by reference.

(c) Other Assay Formats

In an alternative example, the increased methylation in a sample is determined by performing a process comprising treating chromatin containing the nucleic acid with an amount of DNaseI under conditions sufficient for nucleic acid to be digested and then detecting the fragments produced. This assay format is predicated on the understanding that chromatin containing methylated DNA, e.g., hyper methylated DNA, has a more tightly-closed conformation than non-hyper methylated DNA and, as a consequence, is less susceptible to endonuclease digestion by DNase I.

In accordance with this method, DNA fragments of different lengths are produced by DNase I digestion of methylated compared to non-methylated DNA. Such different DNA fragments are detected, for example, using an assay described earlier. Alternatively, the DNA fragments are detected using PCR-SSCP essentially as described, for example, in Gregory and Feil, *Nucleic Acids Res.,* 27, e32i-e32iv, 1999. In adapting PCR-SSCP to the present invention, amplification primers flanking or comprising one or more CpG dinucleotides in a nucleic acid that are resistant to DNase I digestion in a neoplasia sample but not resistant to DNase I digestion in a healthy/normal control or healthy/normal test sample are used to amplify the DNase I-generated fragments. In this case, the production of a specific nucleic acid fragment using DNase I is diagnostic of neoplasia, because the DNA is not efficiently degraded. In contrast, template DNA from a healthy/normal subject sample is degraded by the action of DNase I and, as a consequence, amplification fails to produce a discrete amplification product. Alternative methods to PCR-SSCP, such as for example, PCR-dHPLC are also known in the art and contemplated by the present invention.

(d) Selective Mutagenesis of Non-Methylated DNA

In an alternative method the increased methylation in a sample is determined using a process comprising treating the nucleic acid with an amount of a compound that selectively mutates a non-methylated cytosine residue within a CpG dinucleotide under conditions sufficient to induce mutagenesis.

Preferred compounds mutate cytosine to uracil or thymidine, such as, for example, a salt of bisulfite, e.g., sodium bisulfite or potassium bisulfite (Frommer et al., 1992, supra). Bisulfite treatment of DNA is known to distinguish methylated from non-methylated cytosine residues, by mutating cytosine residues that are not protected by methylation, including cytosine residues that are not within a CpG dinucleotide or that are positioned within a CpG dinucleotide that is not subject to methylation.

Sequence Based Detection

In one example, the presence of one or more mutated nucleotides or the number of mutated sequences is determined by sequencing mutated DNA. One form of analysis comprises amplifying mutated nucleic acid using an amplification reaction described herein, for example, PCR. The amplified product is then directly sequenced or cloned and the cloned product sequenced. Methods for sequencing DNA are known in the art and include for example, the dideoxy chain termination method or the Maxam-Gilbert method (see Sambrook et al., Molecular Cloning, A Laboratory Manual (2nd Ed., CSHP, New York 1989) or Zyskind et al., Recombinant DNA Laboratory Manual, (Acad. Press, 1988)).

As the treatment of nucleic acid with a compound, such as, for example, bisulfite results in non-methylated cytosines being mutated to uracil (and hence thymidine after an amplification process), analysis of the sequence determines the presence or absence of a methylated nucleotide. For example, by comparing the sequence obtained using a control sample or a sample that has not been treated with bisulfite, or the known nucleotide sequence of the region of interest with a treated sample facilitates the detection of differences in the nucleotide sequence. Any thymine residue detected at the site of a cytosine in the treated sample compared to a control or untreated sample may be considered to be caused by mutation as a result of bisulfite treatment. Suitable methods for the detection of methylation using sequencing of bisulfite treated nucleic acid are described, for example, in Frommer et al., 1992, supra or Clark et al., *Nucl. Acids Res.* 22:2990-2997, 1994.

In another method, the presence of a mutated or non-mutated nucleotide in a bisulfite treated sample is detected using pyrosequencing, such as, for example, as described in Uhlmann et al., *Electrophoresis*, 23: 4072-4079, 2002. Essentially this method is a form of real-time sequencing that uses a primer that hybridizes to a site adjacent or close to the site of a cytosine that is methylated. Following hybridization of the primer and template in the presence of a DNA polymerase each of four modified deoxynucleotide triphosphates are added separately according to a predetermined dispensation order. Only an added nucleotide that is complementary to the bisulfite treated sample is incorporated and inorganic pyrophosphate (PPi) is liberated. The PPi then drives a reaction resulting in production of detectable levels of light. Such a method allows determination of the identity of a specific nucleotide adjacent to the site of hybridization of the primer.

Methods of solid phase pyrosequencing are known in the art and reviewed in, for example, Landegren et al., *Genome Res.*, 8(8): 769-776, 1998. Such methods enable the high-throughput detection of methylation of a number of CpG dinucleotides.

A related method for determining the sequence of a bisulfite treated nucleotide is methylation-sensitive single nucleotide primer extension (Me-SnuPE) or SNaPmeth. Suitable methods are described, for example, in Gonzalgo and Jones, 1997, supra, or Uhlmann et al., *Electrophoresis*, 23:4072-4079, 2002. An oligonucleotide is used that hybridizes to the region of a nucleic acid adjacent to the site of a cytosine that is methylated. This oligonucleotide is then used in a primer extension protocol with a polymerase and a free nucleotide diphosphate or dideoxynucleotide triphosphate that corresponds to either or any of the possible bases that occur at this site following bisulfite treatment (i.e., thymine or cytosine). Preferably, the nucleotide-diphosphate is labelled with a detectable marker (e.g. a fluorophore). Following primer extension, unbound labelled nucleotide diphosphates are removed, e.g. using size exclusion chromatography or electrophoresis, or hydrolyzed, using for example, alkaline phosphatase, and the incorporation of the labelled nucleotide to the oligonucleotide is detected, indicating the base that is present at the site.

Clearly other high throughput sequencing methods are encompassed by the present invention. Such methods include, for example, solid phase minisequencing (as described, for example, in Southern et al., *Genomics*, 13:1008-1017, 1992), or minisequencing with FRET (as described, for example, in Chen and Kwok, *Nucleic Acids Res.* 25:347-353, 1997).

Restriction Endonuclease-Based Assay Format

In one method, the presence of a non-mutated sequence is detected using combined bisulfite restriction analysis (COBRA) essentially as described in Xiong and Laird, 2001, supra. This method exploits the differences in restriction enzyme recognition sites between methylated and unmethylated nucleic acid after treatment with a compound that selectively mutates a non-methylated cytosine residue, e.g., bisulfite.

Following bisulfite treatment a region of interest comprising one or more CpG dinucleotides that are methylated and are included in a restriction endonuclease recognition sequence is amplified using an amplification reaction described herein, e.g., PCR. The amplified product is then contacted with the restriction enzyme that cleaves at the site of the CpG dinucleotide for a time and under conditions sufficient for cleavage to occur. A restriction site may be selected to indicate the presence or absence of methylation. For example, the restriction endonuclease TaqI cleaves the sequence TCGA, following bisulfite treatment of a non-methylated nucleic acid the sequence will be TTGA and, as a consequence, will not be cleaved. The digested and/or non-digested nucleic acid is then detected using a detection means known in the art, such as, for example, electrophoresis and/or mass spectrometry. The cleavage or non-cleavage of the nucleic acid is indicative of cancer in a subject. Clearly, this method may be employed in either a positive read-out or negative read-out system for the diagnosis of a cancer.

Positive Read-Out Assay Format

In one embodiment, the assay format of the invention comprises a positive read-out system in which DNA from a sample that has been treated, for example, with bisulfate is detected as a positive signal. Preferably, the non-hypermethylated DNA from a healthy or normal control subject is not detected or only weakly detected.

In a preferred embodiment, the increased methylation in a subject sample is determined using a process comprising:

(i) treating the nucleic acid with an amount of a compound that selectively mutates a non-methylated cytosine residue under conditions sufficient to induce mutagenesis thereby producing a mutated nucleic acid;

(ii) hybridizing a nucleic acid to a probe or primer comprising a nucleotide sequence that is complementary to a sequence comprising a methylated cytosine residue under conditions such that selective hybridization to the non-mutated nucleic acid occurs; and (iii) detecting the selective hybridization.

In this context, the term "selective hybridization" means that hybridization of a probe or primer to the non-mutated nucleic acid occurs at a higher frequency or rate, or has a higher maximum reaction velocity, than hybridization of the same probe or primer to the corresponding mutated sequence. Preferably, the probe or primer does not hybridize to the non-methylated sequence carrying the mutation(s) under the reaction conditions used.

Hybridization-Based Assay Format

In one embodiment, the hybridization is detected using Southern, dot blot, slot blot or other nucleic acid hybridization means (Kawai et al., 1994, supra; Gonzalgo et al., 1997, supra). Subject to appropriate probe selection, such assay formats are generally described herein above and apply mutatis mutandis to the presently described selective mutagenesis approach.

Preferably, a ligase chain reaction format is employed to distinguish between a mutated and non-mutated nucleic acid. Ligase chain reaction (described in EP 320,308 and U.S. Pat. No. 4,883,750) uses at least two oligonucleotide probes that anneal to a target nucleic acid in such a way that they are juxtaposed on the target nucleic acid. In a ligase chain reaction assay, the target nucleic acid is hybridized to a first probe that is complementary to a diagnostic portion of the target sequence (the diagnostic probe) e.g., a nucleic acid comprising one or more methylated CpG dinucleotide(s), and with a second probe that is complementary to a nucleotide sequence contiguous with the diagnostic portion (the contiguous probe), under conditions wherein the diagnostic probe remains bound substantially only to the target nucleic acid. The diagnostic and contiguous probes can be of different lengths and/or have different melting temperatures such that the stringency of the hybridization can be adjusted to permit their selective hybridization to the target, wherein the probe having the higher melting temperature is hybridized at higher stringency and, following washing to remove unbound and/or non-selectively bound probe, the other probe having the lower melting temperature is hybridized at lower stringency. The diagnostic probe and contiguous probe are then covalently ligated such as, for example, using T4 DNA ligase, to thereby produce a larger target probe that is complementary to the target sequence, and the probes that are not ligated are removed by modifying the hybridization stringency. In this respect, probes that have not been ligated will selectively hybridize under lower stringency hybridization conditions than probes that have been ligated. Accordingly, the stringency of the hybridization can be increased to a stringency that is at least as high as the stringency used to hybridize the longer probe, and preferably at a higher stringency due to the increased length contributed by the shorter probe following ligation.

In another example, one or both of the probes is labelled such that the presence or absence of the target sequence can be tested by melting the target-probe duplex, eluting the dissociated probe, and testing for the label(s). Where both probes are labelled, different ligands are used to permit distinction between the ligated and unligated probes, in which case the presence of both labels in the same eluate fraction confirms the ligation event. If the target nucleic acid is bound to a solid matrix e.g., in a Southern hybridization, slot blot, dot blot, or microchip assay format, the presence of both the diagnostic and contiguous probes can be determined directly.

Methylation specific microarrays (MSO) are also useful for differentiating between a mutated and non-mutated sequence. A suitable method is described, for example, in Adorjan et al. *Nucl. Acids Res.*, 30: e21, 2002. MSO uses nucleic acid that has been treated with a compound that selectively mutates a non-methylated cytosine residue (e.g., bisulfite) as template for an amplification reaction that amplifies both mutant and non-mutated nucleic acid. The amplification is performed with at least one primer that comprises a detectable label, such as, for example, a fluorophore, e.g., Cy3 or Cy5.

To produce a microarray for detection of mutated nucleic acid oligonucleotides are spotted onto, for example, a glass slide, preferably, with a degree of redundancy (for example, as described in Golub et al., *Science,* 286:531-537, 1999). Preferably, for each CpG dinucleotide analyzed two different oligonucleotides are used. Each oligonucleotide comprises a sequence $N_2$-16CG$N_2$-16 or $N_2$-16TG$N_2$-16 (wherein N is a number of nucleotides adjacent or juxtaposed to the CpG dinucleotide of interest) reflecting the methylated or non-methylated status of the CpG dinucleotides.

The labelled amplification products are then hybridized to the oligonucleotides on the microarray under conditions that enable detection of single nucleotide differences. Following washing to remove unbound amplification product, hybridization is detected using, for example, a microarray scanner. Not only does this method allow for determination of the methylation status of a large number of CpG dinucleotides, it is also semi-quantitative, enabling determination of the degree of methylation at each CpG dinucleotide analyzed. As there may be some degree of heterogeneity of methylation in a single sample, such quantification may assist in the diagnosis of cancer.

Amplification-Based Assay Format

In an alternative example, the hybridization is detected using an amplification system. In methylation-specific PCR formats (MSP; Herman et al. *Proc. Natl. Acad. Sci. USA* 93:9821-9826, 1992), the hybridization is detected using a process comprising amplifying the bisulfite-treated DNA. Accordingly, by using one or more probe or primer that anneals specifically to the unmutated sequence under moderate and/or high stringency conditions an amplification product is only produced using a sample comprising a methylated nucleotide. Alternate assays that provide for selective amplification of either the methylated or the unmethylated component from a mixture of bisulfite-treated DNA are provided by Cottrell et al., *Nucl. Acids Res.* 32: e10, 2003 (HeavyMethyl PCR), Rand et al. *Nucl. Acids Res.* 33:e127, 2005 (Headloop PCR), Rand et al. *Epigenetics* 1:94-100, 2006 (Bisulfite Differential Denaturation PCR) and PCT/AU07/000389 (End-specific PCR).

Any amplification assay format described herein can be used, such as, for example, polymerase chain reaction (PCR), rolling circle amplification (RCA), inverse polymerase chain reaction (iPCR), in situ PCR (Singer-Sam et al., 1990, supra), strand displacement amplification, or cycling probe technology. PCR techniques have been developed for detection of gene mutations (Kuppuswamy et al., *Proc. Natl. Acad. Sci. USA* 88:1143-1147, 1991) and quantitation of allelic-specific expression (Szabo and Mann, *Genes Dev.* 9: 3097-3108, 1995; and Singer-Sam et al., *PCR Methods Appl.* 1: 160-163, 1992). Such techniques use internal primers, which anneal to a PCR-generated template and terminate immediately 5' of the single nucleotide to be assayed. Such as format is readily combined with ligase chain reaction as described herein above. The use of a real-time quantitative assay format is also useful. Subject to the selection of appropriate primers, such assay formats are generally described herein above and apply mutatis mutandis to the presently described selective mutagenesis approach.

Methylation-specific melting-curve analysis (essentially as described in Worm et al., *Clin. Chem.*, 47:1183-1189, 2001) is also contemplated by the present invention. This process exploits the difference in melting temperature in amplification products produced using bisulfite treated methylated or unmethylated nucleic acid. In essence, non-discriminatory amplification of a bisulfite treated sample is performed in the presence of a fluorescent dye that specifically binds to double stranded DNA (e.g., SYBR Green I). By increasing the temperature of the amplification product while monitoring fluorescence the melting properties and thus the sequence of the amplification product is determined. A decrease in the fluorescence reflects melting of at least a domain in the amplification product. The temperature at which the fluorescence decreases is indicative of the nucleotide sequence of the amplified nucleic acid, thereby permitting the nucleotide at the site of one or more CpG dinucleotides to be determined. As the sequence of the nucleic acids amplified using the present invention The present invention also encompasses the use of real-time quantitative forms of PCR, such as, for example, TaqMan (Holland et al., *Proc. Natl. Acad. Sci. USA,* 88:7276-7280, 1991; Lee et al., *Nucleic Acid Res.* 21:3761-3766, 1993) to perform this embodiment. For example, the MethylLight method of Eads et al., *Nucl. Acids Res.* 28: E32, 2000 uses a modified TaqMan assay to detect methylation of a CpG dinucleotide. Essentially, this method comprises treating a nucleic acid sample with bisulfite and amplifying nucleic acid comprising one or more CpG dinucleotides that are methylated in a neoplastic cell and not in a control sample using an amplification reaction, e.g., PCR. The amplification reaction is performed in the presence of three oligonucleotides, a forward and reverse primer that flank the region of interest and a probe that hybridizes between the two primers to the site of the one or more methylated CpG dinucleotides. The probe is dual labelled with a 5' fluorescent reporter and a 3' quencher (or vice versa). When the probe is intact, the quencher dye absorbs the fluorescence of the reporter due to their proximity. Following annealing of to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. By using a probe or primer that selectively hybridizes to unmutated nucleic acid (i.e. methylated nucleic acid) the level of methylation is determined, e.g., using a standard curve.

Alternatively, rather than using a labelled probe that requires cleavage, a probe, such as, for example, a Molecular Beacon is used (see, for example, Mhlanga and Malmberg, *Methods* 25:463-471, 2001). Molecular beacons are single stranded nucleic acid molecules with a stem-and-loop structure. The loop structure is complementary to the region surrounding the one or more CpG dinucleotides that are methylated in a neoplastic sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

Fluorescently labelled locked nucleic acid (LNA) molecules or fluorescently labelled protein-nucleic acid (PNA) molecules are useful for the detection of nucleotide differences (e.g., as described in Simeonov and Nikiforov, *Nucleic Acids Research,* 30(17):1-5, 2002). LNA and PNA molecules bind, with high affinity, to nucleic acid, in particular, DNA. Fluorophores (in particular, rhodimine or hexachlorofluorescein) conjugated to the LNA or PNA probe fluoresce at a significantly greater level upon hybridization of the probe to target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of a mutated cytosine in a methylated CpG dinucleotide. Preferably, fluorescently labelled LNA or PNA technology is used to detect at least a single base change in a nucleic acid that has been previously amplified using, for example, an amplification method known in the art and/or described herein.

As will be apparent to the skilled artisan, LNA or PNA detection technology is amenable to a high-throughput detection of one or more markers by immobilizing an LNA or PNA probe to a solid support, as described in Orum et al., *Clin. Chem.* 45:1898-1905, 1999.

Alternatively, a real-time assay, such as, for example, the so-called HeavyMethyl assay (Cottrell et al., 2003, supra) is used to determine the presence or level of methylation of nucleic acid in a test sample. Essentially, this method uses one or more non-extendible nucleic acid (e.g., oligonucleotide) blockers that bind to bisulfate-treated nucleic acid in a methylation specific manner (i.e., the blocker/s bind specifically to unmutated DNA under moderate to high stringency conditions). An amplification reaction is performed using one or more primers that may optionally be methylation specific but that flank the one or more blockers. In the presence of unmethylated nucleic acid (i.e., non-mutated DNA) the blocker/s bind and no PCR product is produced. Using a TaqMan assay essentially as described supra the level of methylation of nucleic acid in a sample is determined.

Other amplification based methods for detecting methylated nucleic acid following treatment with a compound that selectively mutates a non-methylated cytosine residue include, for example, methylation-specific single stranded conformation analysis (MS-SSCA) (Bianco et al., *Hum. Mutat.,* 14:289-293, 1999), methylation-specific denaturing gradient gel electrophoresis (MS-DGGE) (Abrams and Stanton, *Methods Enzymol.,* 212:71-74, 1992) and methylation-specific denaturing high-performance liquid chromatography (MS-DHPLC) (Deng et al. *Chin. J. Cancer Res.,* 12:171-191, 2000). Each of these methods use different techniques for detecting nucleic acid differences in an amplification product based on differences in nucleotide sequence and/or secondary structure. Such methods are clearly contemplated by the present invention.

As with other amplification-based assay formats, the amplification product is analyzed using a range of procedures, including gel electrophoresis, gel filtration, mass spectrometry, and in the case of labelled primers, by identifying the label in the amplification product. In an alternative embodiment, restriction enzyme digestion of PCR products amplified from bisulfate-converted DNA is performed essentially as described by Sadri and Hornsby, *Nucl. Acids Res.* 24:5058-5059, 1996; and Xiong and Laird, *Nucl. Acids Res.* 25:2532-2534, 1997, to analyze the product formed.

High throughput detection methods, such as, for example, matrix-assisted laser desorption/ionization time of flight (MALDI-TOF), electrospray ionization (ESI), Mass spectrometry (including tandem mass spectrometry, e.g. LC MS/MS), biosensor technology, evanescent fiber-optics technology or DNA chip technology, can also be employed.

As with the other assay formats described herein that utilize hybridization and/or amplification detection systems, combinations of such processes as described herein above are particularly contemplated by the selective mutagenesis-based assay formats of the present invention. In one example, the increased methylation is detected by performing a process comprising:
(i) treating the nucleic acid with an amount of a compound that selectively mutates a non-methylated cytosine residue within a CpG dinucleotide under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a methylated cytosine residue under conditions such that hybridization to the non-mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a methylated cytosine residue under conditions such that hybridization to the non-mutated nucleic acid occurs; and detecting the hybridization.

Negative Read-Out Assays

In another example, the assay format comprises a negative read-out system in which reduced methylation of DNA from a healthy/normal control sample is detected as a positive signal and preferably, methylated DNA from a neoplastic sample is not detected or is only weakly detected.

In a preferred embodiment, the reduced methylation is determined using a process comprising:
(i) treating the nucleic acid with an amount of a compound that selectively mutates a non-methylated cytosine residue within a CpG island under conditions sufficient to induce mutagenesis thereby producing a mutated nucleic acid;
(ii) hybridizing the nucleic acid to a probe or primer comprising a nucleotide sequence that is complementary to a sequence comprising the mutated cytosine residue under conditions such that selective hybridization to the mutated nucleic acid occurs; and
(iii) detecting the selective hybridization.

In this context, the term "selective hybridization" means that hybridization of a probe or primer to the mutated nucleic acid occurs at a higher frequency or rate, or has a higher maximum reaction velocity, than hybridization of the same probe or primer to the corresponding non-mutated sequence. Preferably, the probe or primer does not hybridize to the methylated sequence (or non-mutated sequence) under the reaction conditions used.

Hybridization-Based Assay Format

In one embodiment the hybridization is detected using Southern, dot blot, slot blot or other nucleic acid hybridization means (Kawai et al., 1994, supra; Gonzalgo et al., 1997, supra). Subject to appropriate probe selection, such assay formats are generally described herein above and apply mutatis mutandis to the presently described selective mutagenesis approach. Preferably, a ligase chain reaction format is employed to distinguish between a non-mutated and mutated nucleic acid. In this respect, the assay requirements and conditions are as described herein above for positive read-out assays and apply mutatis mutandis to the present format. However the selection of probes will differ. For negative read-out assays, one or more probes are selected that selectively hybridize to the mutated sequence rather than the non-mutated sequence.

Preferably, the ligase chain reaction probe(s) have 3'-terminal and/or 5'-terminal sequences that comprise a CpG dinucleotide that is not methylated in a healthy control sample, but is hypermethylated in cancer, such that the diagnostic probe and contiguous probe are capable of being ligated only when the cytosine of the CpG dinucleotide is mutated to thymidine e.g., in the case of a non-methylated cytosine residue.

As will be apparent to the skilled artisan the MSO method described supra is amenable to either or both positive and/or negative readout assays. This is because the assay described detects both mutated and non-mutated sequences thereby facilitating determining the level of methylation. However, an assay detecting only methylated or non-methylated sequences is contemplated by the invention.

Amplification-Based Assay Format

In an alternative example, the hybridization is detected using an amplification system using any amplification assay format as described herein above for positive read-out assay albeit using primers (and probes where applicable) selectively hybridize to a mutated nucleic acid.

In adapting the HeavyMethyl assay described supra to a negative read-out format, the blockers that bind to bisulfate-treated nucleic acid in a methylation specific manner bind specifically to mutated DNA under moderate to high stringency conditions. An amplification reaction is performed using one or more primers that may optionally be methylation specific (i.e. only bind to mutated nucleic acid) but that flank the one or more blockers. In the presence of methylated nucleic acid (i.e., mutated DNA) the blocker/s bind and no PCR product is produced.

In one example, the reduced methylation in the normal/healthy control subject is detected by performing a process comprising:
(i) treating the nucleic acid with an amount of a compound that selectively mutates non-methylated cytosine residues under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a mutated cytosine residue under conditions such that hybridization to the mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a mutated cytosine residue under conditions such that hybridization to the mutated nucleic acid occurs; and
(v) detecting the hybridization.

As will be apparent to the skilled artisan, a negative read-out assay preferably includes a suitable control sample to ensure that the negative result is caused by methylated nucleic acid rather than a reaction failing.

This invention also provides kits for the detection and/or quantification of the diagnostic sequences of the invention, or expression or methylation thereof using the methods described herein.

For kits for detection of methylation, the kits of the invention can comprise at least one polynucleotide that hybridizes to at least one of the diagnostic sequences of the invention and at least one reagent for detection of gene methylation. Reagents for detection of methylation include, e.g., sodium bisulfite, polynucleotides designed to hybridize to sequence that is the product of a biomarker sequence of the invention if the biomarker sequence is not methylated (e.g., containing at least one C→U conversion), and/or a methylation-sensitive or methylation-dependent restriction enzyme. The kits may also include control natural or synthetic DNA sequences representing methylated or unmethylated forms of the sequence. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

The present invention is further described by reference to the following non-limiting examples.

EXAMPLES

Materials and Methods

Specimen Collection

Tissue DNA samples were acquired through a commercial specimen bank (BioServe, @, US) and a tertiary referral hospital tissue bank in Adelaide, Australia. Blood plasma specimens were acquired from a commercial specimen bank (Proteogenex, Culver City, Calif.) and a tertiary referral hospital in Adelaide, Australia. Blood specimens were classified as normal, adenoma or cancer based on colonoscopy results verified (where appropriate) by histopathology. This also identified the stage of the cancer. Peripheral blood was drawn into $K_3$EDTA VACUETTE blood tubes (Greiner-One, Monroe, N.C.) and transported to the processing laboratory on wet ice. Whole blood was centrifuged at 1,500 g (4° C.) for 10 minutes within 4 hours of blood draw and plasma was collected. The plasma was centrifuged for a second time at 1,500 g (4° C.) for 10 minutes, where after the plasma was collected and stored at −80° C. until further use.

Tissue DNA Extraction & Bisulfite Conversion

Tissue specimens were homogenised using a bead homogeniser and genomic DNA extracted using a Wizard® Genomic DNA Purification Kit (Promega, Sydney, Australia).

Commercially acquired DNA was extracted by BioServe (MD, USA). DNA concentration was determined by Nanodrop ND 1000 20 spectrophotometer (Nanodrop Technologies, Wilmington, Del.). The EZ DNA Methylation-Gold Kit (Zymo Research Corporation, Orange, Calif. USA) was used for bisulfite conversion of 1 μmg of tissue-extracted DNA in accordance with the manufacturers instructions with the following modification to the bisulfite reaction cycling conditions: 99° C. for 5 minutes, 60° C. for 25 minutes, 99° C. for 5 minutes, 60° C. for 85 minutes, 99° C. for 5 minutes and 60° C. for 17.5 minutes. The concentration of purified bisulfite converted DNA was determined by qPCR using bisulfite conversion specific primers to beta-Actin [ACTB1], as described in Table 1 and previously by Devos et al. (*Clin. Chem.,* 2009; 55(7):1337-1346). The bisulfite converted DNA samples were stored at −80° C. until further use.

Plasma DNA Extraction & Bisulfite Conversion:

DNA was prepared from 4 mL of plasma using the QIAamp Circulating Nucleic Acid Kit (QIAGEN, Dusseldorf, Germany) according to the manufacturer's specifications with the following modifications: The column was washed twice with 750 ul of ACW2 and twice with 750 ul of absolute ethanol (200 proof). The resulting DNA was eluted in 35 ul of buffer AVE and this eluate was then reapplied to the column and eluted again to increase the concentration of the DNA. The optimised protocol resulted in a 20% improvement in DNA yield compared to the recommended manufacturer protocol (data not shown). The final volume of plasma DNA was ~32 μL per 4 mL of patient plasma. Real-time PCR was used to measure the total DNA recovery: 2×1 μL aliquots of the resulting plasma DNA was used in a previously described CFFI assay (Devon et al. 2009. Clin Chem) (Table 1)

All PCRs were performed on the LightCycler 480 Real-Time PCR System, model H (Roche). A 4-fold serial dilution of sonicated genomic blood DNA (Roche, Mannheim, Germany) was used as a standard to determine the amount (ng) of DNA extracted per mL of plasma 30 μL of DNA extracted from 4 mL plasma was stripped of DNA-binding proteins by incubation at 37° C. for 1 hour after adding 3 uL of a Lysis Buffer consisting of 1 mg/mL tRNA, 2 mg/mL Proteinase K and 10% SDS. The samples were subsequently bisulphite converted using either the EZ DNA Methylation-Gold Kit™ as recommended by the manufacturer (Zymo Research Corp. Orange, Calif. USA), with the same modification to thermal cycling conditions described above, or the Epitect Plus DNA Bisulfite Kit using Epitect Fast bisulfite reagent (QIAGEN, Dusseldorf, Germany) using conditions recommended by the manufacturer. In both cases, the purified DNA was eluted with 40 uL nuclease-free water. The resulting bisulphite DNA concentration was calculated by analysing 2 μL in the ACTB PCR assay as described above. Triplicate 5 uL aliquots of the resulting 36 uL bisulphite converted DNA extracted from 4 mL plasma (the equivalent of 555 μL plasma per aliquot) were analysed in methylation-specific qPCR assays as described below.

Measurement of Methylation

Methylation specific oligonucleotide-primers and probes were designed to interrogate the methylation status of sites within CAHM, GRASP, IRF4, BCAT1 and IKZF1. PCR was performed in triplicate on bisulfite-converted tissue DNA (5 ng) or 5 μL plasma DNA in a total volume of 15 μL (see Table 1 for primer/probe sequences and reaction conditions). Melt peaks of 78.4°+/−0.9° C. (CAHM) and 82.9.4°+/−0.3° C. (IKZF1) were characteristic for the amplicons which ran without a probe. Methylation levels were quantified against an in house made standard curve consisting of a serial dilution of bisulfite-converted sheared methylated DNA (CpGenome Universal Methylated DNA, Chemicon, Temecula, Calif., USA) in a background of sheared bisulfite-converted white blood cell DNA (Roche, Mannheim, Germany). The standard curve contained the following dilution points: 5000-, 1250-, 312.5-, 78.125, 19.53-, 4.88-, 1.22- and 0 pg mCpG in a background of WBC DNA (5 ng total DNA per reaction).

Estimation of Class Probabilities

The R open source programming language and environment for statistical computing and graphics (http://www.r-project.org) was installed on a standard Intel IA-32 personal computer system and used to access and process input data representing the measured methylation levels and corresponding observed non-neoplastic and neoplastic categories, as described below.

Figure 3A:
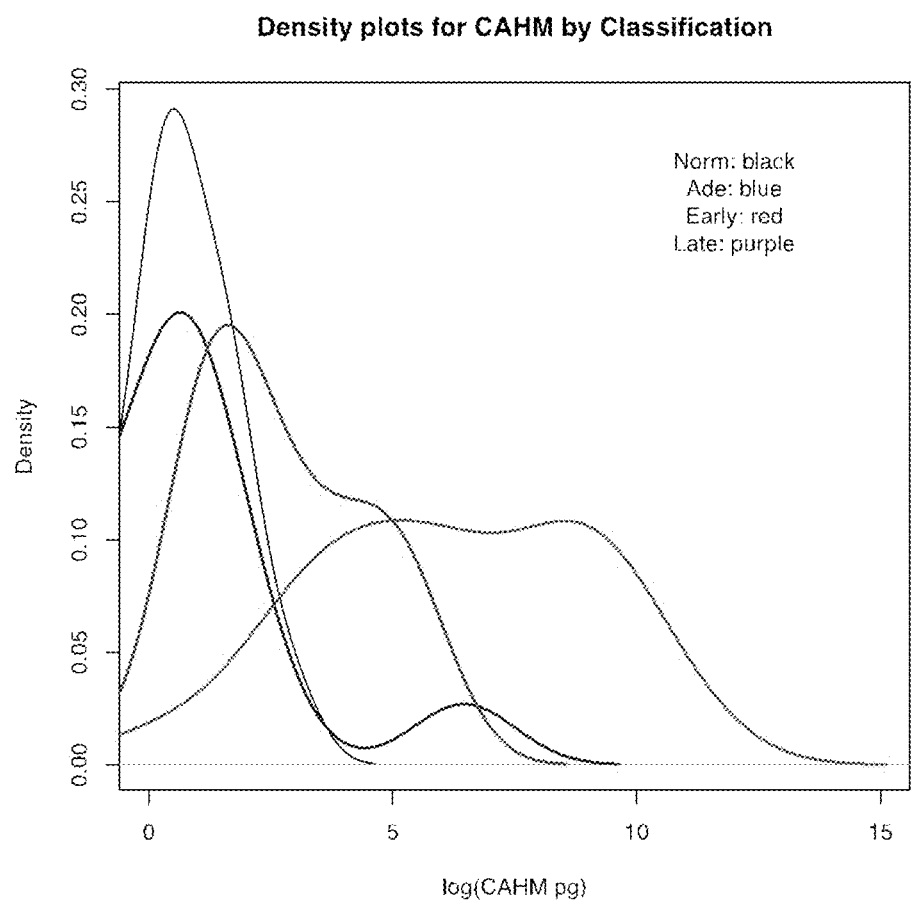
FIG. 3. Density distributions of methylated CAHM grouped by phenotype classification estimated from assay determined methylation levels. A) Empirical probability density curves for CAHM based on methylation levels previously determined by methylated CAHM assays (cf FIG. 1B). Density is estimated using only positive assay values for non-neoplastic plasma specimens (black); premalignant adenomas (blue); early stage cancers including plasma from patients diagnosed with Stage 1 or Stage 2 (red); and late stage cancers including plasma from patients diagnosed with Stage 3 or Stage 4 (purple). B) Estimated normal (Gaussian) distribution using mean and standard deviation estimates determined from positive methylation levels measured in plasma drawn from patients with premalignant neoplastic lesions (blue); early stage cancers (red) and late stage cancers (purple).
Figure 3B:
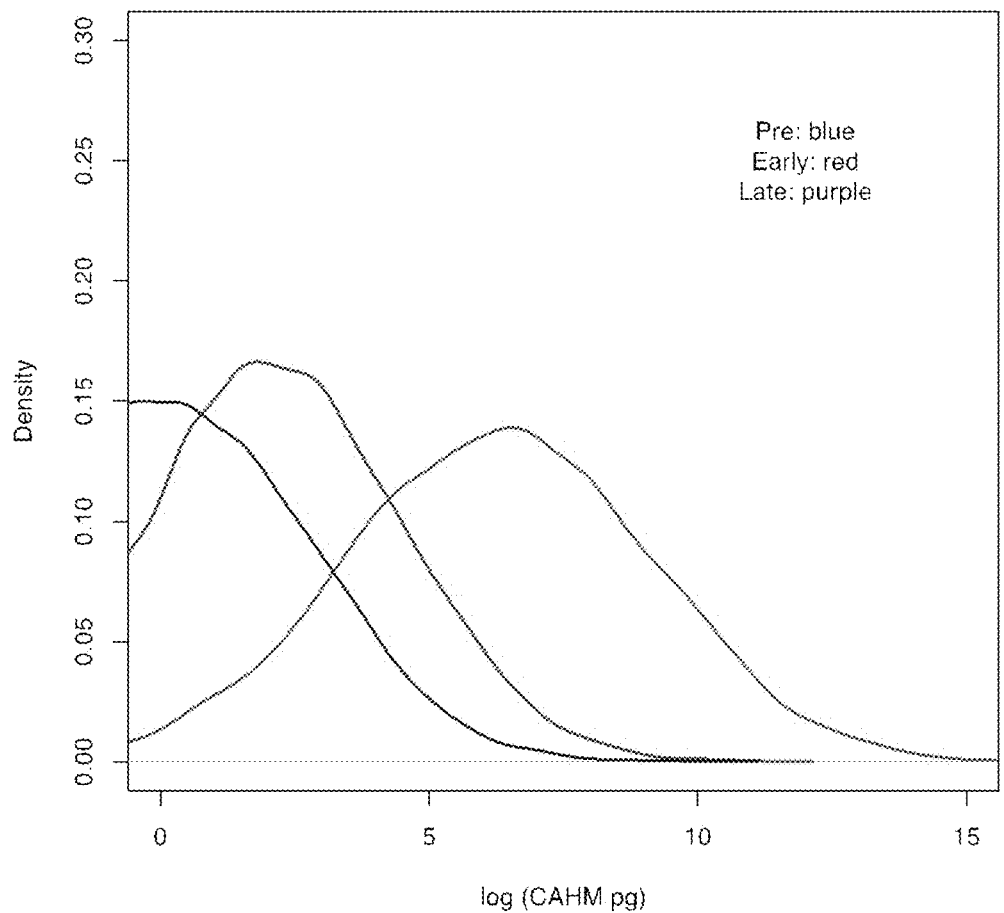

Specifically, the observed methylated CAHM mass by phenotype classification (FIG. 1B) was used to determine the empirical probability density plots for phenotype classes (premalignant, early stage cancer, late stage cancer) (FIG. 3A), and the estimated means and standard deviation values were then used to generate the modelled density plots of FIG. 3B assuming the observed methylation levels are drawn from a normal distribution. The density distributions were then used to estimate the probability that an assayed CAHM methylation level for a patient specimen is drawn from one of these classifications.

Using only positive (i.e., greater than zero) methylation levels determined for plasma specimens of known phenotype (and shown in FIG. 1B), the corresponding estimated distribution profiles are shown in FIG. 3B. These density functions were used to calculate the relative probability that a plasma specimen with a methylated CAHM level of 0.2.8 pg, 148 pg or 22,000 pg is likely to be drawn from a patient diagnosed with colorectal lesions classified as pre-malignant (i.e., adenoma), early-stage cancer (Stage 1 or Stage 2), or late stage cancer (Stage 3 or Stage 4).

| Log (methyl CAHM pg) | RELATIVE Probability (normalised to premalignant) | | |
|---|---|---|---|
| | Pre-malignant | Early-Stage Cancer | Late-Stage Cancer |
| 1.0 (2.8 pg) | 1.0 | 1.0 | 0.175 |
| 5.0 (148 pg) | 1.0 | 3.2 | 4.95 |
| 10.0 (22,000 pg) | 1.0 | 8.3 | 627 |

These data were also used to estimate the probability that a plasma specimen from a known classification would yield an observed methylation level equal to or greater than the hypothetical CAHM methylation levels. Using the probability density functions shown in FIG. 3B and determined from the raw CAHM methylation levels shown in FIG. 1B, it was determined that only 3.0% of premalignant plasma specimens are found to contain at least 148 pg methylated CAHM, while 66% late stage cancers show 148 pg methylation or more (relative value of 23:1): Further, a plasma specimen yielding 22 ng of methylated CAHM is approximately 1600 times more likely to be drawn from a patient with late cancer than a patient with a premalignant neoplasm.

| Log (methyl CAHM pg) | Cumulative probability methylated CAHM is greater than or equal to (ratio to premalignant) | | |
|---|---|---|---|
| | Pre-malignant | Early-Stage Cancer | Late-Stage Cancer |
| 1.0 | 36% (1.0) | 68% (1.8) | 96% (2.6) |
| 5.0 | 3% (1.0) | 12% (4.1) | 66% (23.2) |
| 10.0 | 0.0058% (1.0) | 0.052% (8) | 9% (1600) |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Oligonucleotide sequences and reaction conditions for PCR, Methylation Specific PCR and Methylight assays.

| PCR | Primer/Probe Sequence | Mastermix | Cycling Conditions |
|---|---|---|---|
| CAHM | Foward: GAAGGAAGTATTTCGAGTACG ATTGAC (SEQ ID NO: 9)<br>Reverse: CCCGAACGCAACGACTTAA (SEQ ID NO: 10) | Each 15 µL reaction contained: 0.1 µL 5U/µL Platinum Taq DNA polymerase (Invitrogen), 1.5 µL 10x Platinum Buffer (Invitrogen), 0.9 µL 50 mM MgCl$_2$ (f 3 mM Final, Invitrogen), 0.3 µL 10 mM dNTPs (200 uM Final, Promega), 0.1 µL of the foward and reverse primers (50 uM/200 nM Final) and 0.125 µL 1/1000 SYBR Green and Nuclease Free Water | Activation - 95° C. 2 min.<br>3 Cycles: 92° C. 15 sec (4.4° C./sec), 62° C. 15 sec (2.2° C./sec), 72° C. 20 sec<br>50 Cycles: 82° C. 15 sec (4.4° C./sec), 63° C. 15 sec (2.2° C./sec) 72° C. 20 sec<br>Cooling - 40° C. 5 sec (2.2° C./sec) followed by a Melt analysis to confirm correct product |
| GRASP | Foward: CGGAAGTCGCGTTCGTC (SEQ ID NO: 11)<br>Reverse: GCGTACAACTCGTCCGCTAA (SEQ ID NO: 12)<br>Probe: [HEX] TTCGATTTCGGGATTTTTTGTCGTAGTC [BHQ1] (SEQ ID No: 13) | Each 15 µL reaction contained: 0.1 µL 5U/µL Platinum Taq DNA polymerse (Invitrogen), 1.5 µL 10x Platinum Buffer (Invitrogen), 1.2 µL 50 mM MgCl$_2$(4 mM Final, Invitrogen), 0.3 µL 10 mM dNTPs (0.2 mM Final, Promega), 0.06 µL of the foward and reverse primers (50 uM/200 nM Final) and 0.03 uL of probe (50 uM stock/100 nM Final) | Activation - 95° C. 2 min.<br>3 Cycles: 92° C. 15 sec (4.4° C./sec), 64° C. 15 sec (2.2° C./sec), 72° C. 20 sec (4.4° C./sec)<br>47 Cycles: 85° C. 15 sec (4.4° C./sec), 64° C. 15 sec (2.2° C./sec), 72° C. 20 sec (4.4° C./sec)<br>cooling - 40° C. 10 sec (2.2° C./sec). |

TABLE 1-continued

Oligonucleotide sequences and reaction conditions for PCR, Methylation Specific PCR and Methylight assays.

| PCR | Primer/Probe Sequence | Mastermix | Cycling Conditions |
|---|---|---|---|
| IRF4 | Foward: TGGGTGTTTTGGACGGTTTC (SEQ ID No: 14)<br>Reverse: CGCCTACCCTCCGCG (SEQ ID No: 15)<br>Probe:[HEX]) TCGTTTAGTTTGTGGCGATTTCGTCG {BHQ1] (SEQ ID No: 16) | Each 15 µL reaction contained: 0.1 µL 5U/µL Platinum Taq DNA polymerse (Invitrogen), 1.5 µL 10x Platinum Buffer (Invitrogen), 1.2 µL 50 mM MgCl$_2$(4 mM Final, Invitrogen), 0.3 µL 10 mM dNTPs (0.2 mM Final, Promega), 0.12 µL of the foward and reverse primers (50 uM/200 nM Final) and 0.03 uL of probe (10 uM stock/200 nM Final) | Activation - 95° C. 2 min.<br>3 Cycles: 92° C. 15 sec (4.4° C./sec), 64° C. 15 sec (2.2° C./sec), 72° C. 30 sec (4.4° C./sec)<br>50 Cycles: 86° C. 15 sec (4.4° C./sec), 62° C. 30 sec (2.2° C./sec), 72° C. 30 sec (4.4° C./sec) cooling - 40° C. 10 sec (2.2° C./sec). |
| BCAT1 | Foward: GTTTTTTTGTTGATGTAATTCGTTAGGTC (SEQ ID No: 17)<br>Reverse: CAATACCCGAAACGACGACG (SEQ ID No: 18)<br>Probe:HEX-5' TTCGTCGCGAGAGGGTCGGTT-BHQ (SEQ ID No: 19) | Each 15 µL reaction contained: 0.1 µL 5U/µL Platinum Taq DNA polymerse (Invitrogen), 1.5 µL 10x Platinum Buffer (Invitrogen), 1.2 µL 50 mM MgCl$_2$(4 mM Final, Invitrogen), 0.3 µL 10 mM dNTPs (0.2 mM Final, Promega), 0.06 µL of the foward and reverse primers (50 uM/200 nM Final) and 0.15 uL of probe (10 uM stock/100 nM Final) | Activation - 95° C. 2 min.<br>50 Cycles: 95° C. 15 sec (4.4° C./sec), 62° C. 30 sec (2.2° C./sec), 72° C. 30 sec (4.4° C./sec) cooling - 40° C. 5 sec (2.2° C./sec). |
| IKZF1 | Foward: GACGACGTATTTTTTTCGTGTTTC (SEQ ID No: 20)<br>Reverse: GCGCACCTCTCGACCG (SEQ ID No: 21) | Each 15 µL reaction contained: 7.5 µL of 2x GoTaq Hot Start buffer w/MgCL2, 0.3 µL 50 mM MgCl$_2$ (4 mM Final, Invitrogen), 0.06 µL of the foward and reverse primers (50 uM/200 nM Final) and 0/15 ul of SYBR (1:1000 stock/1: 100,000 Final) | Activation - 95° C. 2 min.<br>50 Cycles: 95° C. 15 sec (4.4° C./sec), 62° C. 30 sec (2.2° C./sec), 72° C. 30 sec (4.4° C./sec) cooling - 40° C. 5 sec (2.2° C./sec). |
| CFF1 | Foward: TAAGAGTAATAATGGATGGAT GATG (SEQ ID No: 22)<br>Reverse: CCTCCCATCTCCCTTCC (SEQ ID No: 23)<br>Probe: 6FAM-ATGGATGAAGAAAGAAAGGATGAGT-BHQ-1 (SEQ ID No: 24) | Each 15 µL reaction contained: 0.15 µL 5U/µL Platinum Taq DNA polymerse (Invitrogen), 1.5 µL 10x Platinum Buffer (Invitrogen), 0.9 µL 50 mM MgCl$_2$ (3 mM Final, Invitrogen), 0.3 µL 10 mM dNTPs (0.2 mM Final, Promega), 0.189 µL of the foward and reverse primers (50 uM/200 nM Final) and 0.3 uL of probe (10 uM stock/200 nM Final) | Activation - 95° C. 2 min.<br>50 Cycles: 95° C. 10 sec (4.4° C./sec), 58° C. 60 sec (2.2° C./sec) cooling - 40° C. 5 sec (2.2° C./sec). |

TABLE 1-continued

Oligonucleotide sequences and reaction conditions for PCR, Methylation Specific PCR and Methylight assays.

| PCR | Primer/Probe Sequence | Mastermix | Cycling Conditions |
|---|---|---|---|
| β-actin | Foward: GTGATGGAGGAGGTTTAGTAAGTT (SEQ ID No: 25)<br>Reverse: CCAATAAAACCTACTCCTCCCTTAA (SEQ ID No: 26)<br>Probe: FAM-ACCACCACCCAACACACAATAAC AAACACA-BHQ1 (SEQ ID No: 27) | Each 15 μL reaction contained: 0.15 μL 5U/μL Platinum Taq DNA polymerse (Invitrogen), 1.5 μL 10x Platinum Buffer (Invitrogen), 0.6 μL 50 mM $MgCl_2$ (2 mM Final, Invitrogen), 0.3 μL 10 mM dNTPs (0.2 mM Final, Promega), 0.27 μL of the foward and reverse primers (50 uM/900 nM Final) and 0.15 uL of probe (10 uM stock/100 nM Final) | Activation - 95° C. 2 min.<br>60 Cycles: 95° C. 10 sec (4.4° C./sec), 57° C. 40 sec (2.2° C./sec) 10 sec (4.4° C./sec) cooling - 40° C. 5 sec (2.2° C./sec). |

TABLE 2

| Gene | Genomic Strand | Current sub-region(s) of interest (genomic sequence) | Coordinates of sub region(s) | Resulting bisulphite converted sequence (strands no longer complementary) | Oligonucleotide sequences for measurement of methylation levels |
|---|---|---|---|---|---|
| BCAT1 | top strand | 5'-cagtgccCGaggCGgcCGgcCGagtacaCGtggCGgctggattgcagacCGgccctctCGCGgCGgagactCGCgaactagCGgattgcatcagcaggaagac (SEQ ID No: 1) | 25,101,992-25,102,093 | 5'-tagtgttCGaggCGgcCGgcCGagtataCGtggCGggttggattagatCGgttttttCGCGgCGgagattCGCGattagCGgattgattagtaggaagat (SEQ ID No: 28) | 5'-gtttttttgttGtgtaattcgttaggtc (SEQ ID No: 31) |
|  | minus strand | 3'-gtcacggGCtccGCcGCcGCctcatgtGCaccGCccgaactaacgtctgGCcgggagaGCGCcGCcctcgaGCGCtggatcGCctaacgtagtcgtccttctg (SEQ ID No: 29) |  | 3'-gttatggGCttGCtGCtGCtGCttatgtGCattGCttgatttaatgtttgGCtgggagaGCGCtGCttttttgaGCGCtggatGCttaatgtagttgttttttg (SEQ ID No: 30) | 5'-caataccgaaacgacgacg (SEQ ID No: 32) 5'-ttcgtcgcgagagggtcggtt (SEQ ID No: 33) 5'-tttttttgatgtaattcgttaggtc (SEQ ID No: 34) 5'-attacaaaccgaccctctcg (SEQ ID No: 35) |
|  | top strand | 5'-agatcccaagggtCGtagccctggcCGtgtggacCGggtctgCGgctgcagagCGCGgtccCGgctgcagcaagactgggggcagt ((SEQ ID No: 2) | 25,101,909-25,101,995 | This sequence is for measuring CpG methylation levels using methylation sensitive restriction enzymes (e.g. HhaI, HhaI (underlined)) | 5'-agatcccaagggtcgtagc (SEQ ID No: 36) 5'-actgcccccaggtcttgct (SEQ ID No: 37) |
|  | minus strand | 3'-tctagggttcccaGCatcggggaccgGCacacctgGCccagaGCcgacgtctcGCGCcaggGCcgacgtcgttctgaaccccgtca (SEQ ID No: 38) |  |  |  |
| IKZF1 | top strand | 5'-gaCGaCGcaccctctCGtgtccCGctctgCGccttctgCGGCgcccCGctcctgtacCGgagcagCGatcCGggaggCGgcCGagaggtgCGc (SEQ ID No: 3) | 50,343,867-50,343,961 | 5'-gaCGaCGtattttttCGtgttCGtgttttttgCGCGtttCGtttttgtatCGgagtagCGgattCGgaggCGgtCGagaggtgCGt (SEQ ID No: 39) | 5'-gacgacgtattttttcgtgttc (SEQ ID No: 40) 5'-gcgcacctccgaccg (SEQ ID No: 41) 5'-ttgtatcggagtagcgattccgggag (SEQ ID No: 42) |
|  | minus strand | 3'-ctGCtGCgtgggagagGCacaggGCgagaCGCgggaagacGCGCgggGCgagggacatgGCGCctgctgCtagGCcctccGCccgGCtctccacGCg (SEQ ID No: 43) | 50,343,804-50,343,895 | 3'-ttGCtGCgtgggagagGCataggGCgagatGCgggaagatGCgggGCgagggatatgGCtttgttGCtaggGCttttGCtgGCtttttatGCg (SEQ ID No: 44) |  |
|  | top strand | 5'-CGgagttgCGgctgagaCGCGCGcCGCGCgaCGggact CGgCGaCGggcCGggCGCGggCGagCggaCGgaCGcaccctctCGtgtccCGctct (SEQ ID No: 4) |  | This sequence is for measuring CpG methylation levels using methylation sensitive restriction enzymes (e.g. HhaI, HhaI (underlined)) | 5'-ggagttgcggctgagac (SEQ ID No: 45) 5'-agagcggaacgggaga (SEQ ID No: 46) |
|  | minus strand | 3'-gGCctcaacGCcgactctGCGCGCggGCGCGCtcgGCcccctgaGCcGCtGCcccGCcctGCcctGCtGCgtgggagGCacaggGCgaga (SEQ ID No: 47) |  |  |  |
| IRF4 | top strand | 5'-CGcctgccctcCGCGctcctgCGaCGggtCGccacagctggaCGggatgagctaacCgactgtCGggcccccaggagtggctgaggCGggcCGtccaaggcacca (SEQ ID No: 5) | 392,036-392,145 | 5'-CGttttgttttCGCGttttttgCGaCGgggtCGttataagttggaCGggatagagttatCGgattgtCGgggttttaggagttgaggCGgggtCGttaaggtattta (SEQ ID No: 48) | 5'-gtttttgcgacggggtc (SEQ ID No: 49) 5'-taaaacccgacaatccg (SEQ ID No: 50) |

TABLE 2-continued

| Gene | Genomic Strand | Current sub-region(s) of interest (genomic sequence) | Coordinates of sub region(s) | Resulting bisulphite converted sequence (strands no longer complementary) | Oligonucleotide sequences for measurement of methylation levels |
|---|---|---|---|---|---|
| | minus strand | 3'-GCggacggagGCGCgaggacGCtGCcccaGCggtgtcgacctGCcctactcgattgGCctgacaGCcccgggtcctcaccgactccGCcccgGCaggttcgtgggt (SEQ ID No: 51) | | 3'-GCggatgggagGCGCgaggatGCtGCtttaGCggtgtttgattGCttattgatgGCttgataGCtttgggttttattgattGCtttgGCaggtttgtgggt (SEQ ID No: 52) | 5'-tgggtgtttttggacggttc (SEQ ID No: 53)<br>5'-tagttattttggggtttcgatagttc (SEQ ID No: 54)<br>5'-cgcctaccctccgcg (SEQ ID No: 55)<br>5'-tgtttagtttgtgggatttcgtcg (SEQ ID No: 56) |
| GRASP | top strand | 5'-caggaagctgcagcagaaggaggaggCGgCCtgcacccCCtgaccCCtcCCccCCggacteeCCactCGgaagtCGCgccCGccCGctcCGgtccCGacccCGggaccccctgcGCcagcCGccacctggcccccagCCgaCtagctgtaCGcGgCCgctgaaagactatcaccgtcCGagctgtacCGCGCGctCgcCGtgtcCGggcacecgcecCCgcCGaaaggtgCGtccccCGccGcccttcaggatctgtcagcccctctcCGactccctacagggcctgctgactcCG (SEQ ID No: 6) | 52,400,821-52,401,051 | 5'-taggaagtgtagtagaaggaggaggCCgcCGgttattCGgattCGtCGttCGgttCGgttttCGattCGgaagtCGCGttCGaactCGgcccCGccCCGgtccCGactCGtattttgggttttaCGgaCGagttgtaCGCGCgCgttgaggattattaatttgtCGagtgtatCGCGCGttCGttCGgttCGggggtattgttCGtCGaaaggtgCGtttttCGttCGttttaggattgtttagttttttCGattttttataggtttgttgatttCG (SEQ ID No: 57) | 5'-cggaagtcgcgttcgtc (SEQ ID No: 58)<br>5'-gcgtacaactcgtccgctaa (SEQ ID No: 59)<br>5'-ttcgatttcgggattttttgtcgtagtc (SEQ ID No: 60)<br>5'-cggattttcgattcggaagt (SEQ ID No: 61) |
| | minus strand | 3'-gtccttcgacgtgtcttcctctccGCcGCcggttgggGCctgggGCgGCggGCctgaggGCtgaGCcctcacGCGCggGCgGCgagGCcaggGCtgggGCcctggggaacGCgtcgGCggtgggaacccggagggtoGCctGCtcgacatGCGCGCgacctctgataagtgggacgGCtcgacatgGCGCGCgaGCGCgCacagGCccccgtggacggGCgGCtttccacGCcaggGCGGCggGCtgaagtctagacgagtcgggagagGCtgagggatgtccccggacgactgagGC (SEQ ID No: 62) | | 3'-gttttttgatgtgtattttttGCtGCtggtgggGCttgggGCgGgggGCttgaggGCtgaGCtttaGCGCggGCgGCgagGCtaggGCttgggGCtttggggatggGCgttgGCggtgggatttgggggtGCtgtGCttgatatGCGCtGCgatttatgatagtgggatGCttgatatgCGCGCggaGCgGCataagGCttttgtgggatgggGCgGCtttgatGCagggGCgGCggaagttttagtagttgaggataggggatgttccccggacgactgaggGC (SEQ ID No: 63) | 5'-ggtagggtgttttcggatac (SEQ ID No: 64)<br>5'-aacgaacgaactatacgcgac (SEQ ID No: 65) |
| | top strand | 5'-gacagagacagcccaggcaagttgaaggtcCGagagccccCGgtgggagaagCGggcCGtgctgCGcCGCGtgCGttctcactctgaggaagtgCGtggagcCGgctgactcCGgattgcacccctcCGaggggactccCGattcctggggcgcCGggcctgccccaCGtctgaCGtaCGggGCGGCgagggccactgtccctggactCGtCGgaacCGgaCGcagtgggagggtCGcagg (SEQ ID No: 66) | 52,401,407-52,401,664 | 5'-gataagatataggttaggtaagttgaaggttCGagagttttCGgtggagaagCGggtCGgtggttgCGtCGCGtgCGttttatttgaggaagtCGtggggagtCGtgattCGgatagtatattttCGaggggatttCGatttttgggttgggGtgtCGtttgtttttaCGtttgaCGtaCGgggCGGaggggttattgttttttggattttgtCGgaatCGgaCGtagtgggaaggggtCGtagg (SEQ ID No: 66) | |
| | minus strand | 3'-ctgtctctgggagtccgttcaacttccagGCtctcggggGCcacctcttcGCccgGCcaccgacGCgGCGCacGCaagagtgagactccttcacGCcaccctgGCgactgagGC | | 3'-ttgttttgtgggttgttaatttagGCttttgggGCtattttttGCttgGCtattgatGCgGCGCatGCaagaagttagaattttttatGCatttttgGCgattgagGCtattgtgggaaGCttttgag | 5'-cggagttagcggttttacg (SEQ ID No: 69)<br>5'-cgataaaaaaacgaaccga (SEQ ID No: 70) |

TABLE 2-continued

| Gene | Genomic Strand | Current sub-region(s) of interest (genomic sequence) | Coordinates of sub region(s) | Resulting bisulphite converted sequence (strands no longer complementary) | Oligonucleotide sequences for measurement of methylation levels |
|---|---|---|---|---|---|
| | | ctatcgtgtgggaagGCtcccctgagggG CtaaggacccgaccccggacgGCggacg gggtGCagactGCatGCcccGCGCtccgg tgacgaaggaactgaagacaGCcttgGCct GCgtcaccctcccaGCgtcc (SEQ ID No: 67) | | ggGCtaaggatttgattttgatgGCggattgggat GCagattGCatGCtttGCGCttttggtgatgaggat ttgaagataGCtttgGCttGCgttattttttaGCg ttt (SEQ ID No: 68) | 5'-agagtgagaacgtacgcggc (SEQ ID No: 71) |
| | top strand | 5'-gacagagacgcccaggcaagttgaa ggtcCGagagcccCGgtggagaagCGggc CGgtggctgCGgCGCGCgCGttctcactct gaggaagtgCGtggggagcCGctgactgCG gattagcacaccctcCGagggggactcccCG attcctgggctggggcctgcCGcctggcc ccaCGtctgaCGtaCGggGCGCGaggggcca ctgctccctgactctgtCGgaacCGgaaC Gcagtggaggggtgggt (SEQ ID No: 72) | | This sequence is for measuring CpG methylation levels using methylation sensitive restriction enzymes (e.g. HhaI, HhaI (underlined) | 5'-caagttgaaggtccgagagc (SEQ ID No: 73) 5'-cgcacttcctcagagtgaga (SEQ ID No: 74) |
| | minus strand | 3'-ctgtctctgtcgggtccgttcaactt ccagGCtctcggggGCcaccctctcGCcc gGCcaccgacGCgGCGCacGCaagagtgag actcttcacGCaccccctcgGCgactgagG CctatcgtgtggaagGCtcccctgagggG Ctaaggacccgaccccggacgggcggacg gggtGCagactGCatGCcccGCGCtccgg tgacgagggaactgaagacaGCcttgGCct GCgtcaccctcccaGCgtcc (SEQ ID No: 75) | | | |
| CAHM | top strand | 5'-atctgtaaaaatgttgactctgcttt tcagactaCGCGcacgcctcttatttcc tactCGgcttcattccctcaCCGgaacactg acGgccatCGCGaaggaagcatttCGagcaC GactaCGctcccattattgctaagc CGctgCGctCGggtctggctaCGatttgct ttcagaataaCGggaaggtcaacaaga (SEQ ID No: 8) | 163,834,295 163,834,500 | 5'-atttgtaaaaatgttgattttgttttttagatt aCGCGtatagtttttattttttattgCGgttttat ttttttaCGgaatattgaCGttatCGCGaaggaagta tttCGagtaCGattgaCGttttttatttattgtta agtCGttgCGttCGggtttggttaCGatttgttttta gaataaCGggaaggtgtaataaga (SEQ ID No: 76) | 5'-gaaggaagtatttcgagtacgacttaa (SEQ ID No: 77) 5'-cccgaacgcaacgacttaa (SEQ ID No: 78) 5'-gcctctaaaaaacgatcttattaccac (SEQ ID No: 79) |
| | minus strand | 3'-tagacatttttacaactgaagacgaaa agtcgatGCGCgtgttggagaaataaaggatGCgtgaagta | | 3'-tagatattttttataattgaagatgaaaaagtttga tGCGCgtgttggagaaataaaggatgGCtgaagta | 5'-gaaacactaacgcatcg (SEQ ID No: 82) |

TABLE 2-continued

| Gene | Genomic Strand | Current sub-region(s) of interest (genomic sequence) | Coordinates of sub region(s) | Resulting bisulphite converted sequence (strands no longer complementary) | Oligonucleotide sequences for measurement of methylation levels |
|---|---|---|---|---|---|
| | | tgacGCcgaagtaagggagtGCcttgtgac tGCggtaGCGCttccttcgtaaaGCtcgtG CtgactGCgagggaataataaacgattcg GCgacGCgaGCccagaccgatGCtaaacga aagtcttattGCccttccacgttgttct (SEQ ID No: 80) | | agggagtGCttttgtgattGCggtaGCGCttttttgtaa aGCtgtGCtgattGCgagggaataataatgattt gGCgatGCgaGCttagattgatGCtaaatgaaagttt tattGCttttttatgttgttt (SEQ ID No: 81) | 5'-cgtagttagattcgagcgtag (SEQ ID No: 83) 5'-aggggagcgttagtcgtgttcgaaa (SEQ ID No: 84) |
| | minus strand | 3'-cgGCacgacgaaagtcgagagtcgt ttagtGCttgtgGCtttcttcggtGCcGCc GCtGCcctccccGCaGCGCGCacgaaggga GCcGCtgttcGCcctcgGCccgGCcGCgGCc gGCtcccGCggGCcGCgtctcaggGCgtct ccGCctGCgGCGCcgtGCgGCggaGCttttc ggagtttgagaataggaGCcgagaggGCgg ggtgagGCgggGCgtcggttctggGCGCg GCaccGCccggGCtGCcggttccttttcgg tggtcgggagGCtgGCac (SEQ ID No: 85) | 163,834,621 163,834,906 | tgGCatgatgaaagttgagagttgttagtGCttg tgGCtttttgtGCtGCtGCtttttGCaGC GCGCatgaaaggaGCtGCtgttttGCtttgGCtGCG CgGCtgGCtttGCggGCtGCgtttaggGCgtttt GCttGCgGCGCgtGCGCggaGCttttggagttga gaataggaGCtgagaggGCgggtggagGCgggGCgt tggttttggGCGCgGCattGCttggGCtGCtggttt ttttggtggtgggagGC tgGCat (SEQ ID No: 86) | 5'-gtttttttcggcgataaagc (SEQ ID No: 87) 5'-cgcctctacgaaactctacg (SEQ ID No: 88) 5'-cgtcggtcgagggcgttc (SEQ ID No: 89) |

BIBLIOGRAPHY

Adorjan et al. *Nucl. Acids. Res.*, 30: e21, 2002
Ammerpohl et al. *Biochim Biophys Acta.* 1790:847-62, 2009
Beaucage, et al. *Tetrahedron Letters* 22:1859-1862, 1981
Caruthers, M. H., et al., *Methods in Enzymology*, Vol. 154, pp. 287-314 (1988)
Chen and Kwok, *Nucleic Acids Res.* 25:347-353, 1997
Clark et al. *Nat Protoc.* 1:2353-64, 2006
Cottrell et al., *Nucl. Acids Res.* 32: e10, 2003
DeGraves, et al., *Biotechniques* 34(1):106-10, 112-5 (2003)
Deiman B, et al., *Mol. Biotechnol.* 20(2):163-79 (2002)
Devos et al. (*Clin. Chem.*, 2009; 55(7):1337-0.1346
Eads et al., *Cancer Res.* 59:2302-2306 (1999)
Eads et al., *Nucl. Acids Res.* 28: E32, 2000
Egholm et al., *Am. Chem. Soc.*, 114:1895, 1992
Egholm et al., *Nature*, 365:566, 1993
Fodor et al., *Science* 767-773, 1991
Frommer et al., *Proc. Natl. Acad. Sci. USA* 89:1827-1831 (1992)
Gibson et al., *Genome Research* 6:995-1001 (1996)
Golub et al., *Science*, 286:531-537, 1999
Gonzalgo & Jones, *Nucleic Acids Res.* 25:2529-2531 (1997)
Gonzalgo et al., *Cancer Res.* 57:594-599, 1997
Gregory and Feil, *Nucleic Acids Res.*, 27, e32i-e32iv, 1999
Herman et al. *Proc. Natl. Acad. Sci. USA* 93:9821-9826, 1992
Holland et al., *Proc. Natl. Acad. Sci. USA*, 88:7276-7280, 1991
Kawai et al., *Mol. Cell. Biol.* 14:7421-7427, 1994
Kristensen and Hansen *Clin Chem.* 55:1471-83, 2009
Kuppuswamy et al., *Proc. Natl. Acad. Sci. USA* 88:1143-1147, 1991
Landegren et al., *Genome Res.*, 8(8): 769-776, 1998
Lee et al., *Nucleic Acid Res.* 21:3761-3766, 1993
Markowitz and Bertagnolli (2009). *N. Engl. J. Med.* 361 (25):2449-60
Messing, *Methods Enzymol*, 101, 20-78, 1983
Mhlanga and Malmberg, *Methods* 25:463-471, 2001
Narang, et al. *Meth. Enzymol* 68: 90, 1979
Nielsen et al. *J. Chem. Soc. Perkin Trans.*, 1:3423, 1997
Olek, et al. *Nat. Genet.* 17(3): 275-6 (1997)
Orum et al., *Clin. Chem.* 45:1898-1905, 1999
Orum et al., *Nucl. Acids Res.*, 21:5332, 1993
Rand et al. *Epigenetics* 1:94-100, 2006
Rand et al. *Nucl. Acids Res.* 33:e127, 2005
Rein, et al. *Nucleic Acids Res.* 26 (10): 2255-64 (1998)
Sadri and Hornsby, *Nucl. Acids Res.* 24:5058-5059, 1996
Sambrook et al., Molecular Cloning, A Laboratory Manual (2nd Ed., CSHP, New York 1989)
Shames et al. *Cancer Lett.* 251:187-98, 2007
Simeonov and Nikiforov, *Nucleic Acids Research*, 30(17): 1-5, 2002
Singer-Sam et al., *Nucl. Acids Res.* 18:687, 1990
Singer-Sam et al., *PCR Methods Appl.* 1: 160-163, 1992
Singh and Wengel, *Chem. Commun.* 1247, 1998
Southern et al., *Genomics*, 13:1008-1017, 1992
Szabo and Mann, *Genes Dev.* 9: 3097-3108, 1995
Toyota et al., *Cancer Res.* 59:2307-12 (1999)
Uhlmann et al., *Electrophoresis*, 23: 4072-4079, 2002
Worm et al., *Clin. Chem.*, 47:1183-1189, 2001
Xiong and Laird, *Nucl. Acids Res.* 25:2532-2534, 1997
Zyskind et al., Recombinant DNA Laboratory Manual, (Acad. Press, 1988)

---

The invention claimed is:

1. A method comprising measuring a methylation level of a DNA region of a sample from an individual having or suspected of having a large intestine neoplasm, wherein said measuring of a methylation level of a DNA region of a sample from said individual comprises:
   selecting an individual from a patient population known or suspected to have a large intestine neoplasm staged as adenoma, stage I, stage II, stage III, or stage IV;
   obtaining or having obtained a blood-derived sample from said individual, the blood-derived sample comprising circulating cell-free DNA;
   extracting circulating cell-free DNA from the sample;
   bisulfite converting the circulating cell-free DNA; and
   detecting a level of methylation of a DNA region of the bisulfite converted DNA, wherein said detecting comprises hybridizing methylation-specific oligonucleotide primers to the DNA region of the bisulfite converted DNA, wherein the DNA region comprises:
   (i) the region, including 2kb upstream of the transcription start site, defined by chr12:24962958 . . . 25102393 and at least one of Hg19 coordinates:
   (1) chr7:50344378 . . . 50472798;
   (2) chr6:391739 . . . 411443;
   (3) chr12:52400748 . . . 52409671; or
   (4) chr6:163834097 . . . 163834982; or
   (ii) the gene region, including 2kb upstream of BCAT1 and at least one of:

| (1) IKZF1; | (2) IRF4; | (3) GRASP; or | (4) CAHM; | determining a probability whether said individual has a premalignant neoplasm, an early stage malignant neoplasm or a late stage malignant neoplasm from said measurement of said methylation level of said DNA region of said sample from said individual.

2. The method of claim 1, wherein said methylation level is measured in
   (1) BCAT1 subregions chr12:25101992-25102093 (SEQ ID NO:1 or corresponding minus strand) and chr12:25101909-25101995 (SEQ ID NO:2 or corresponding minus strand), and one or more chromosomal subregions selected from:
   (2) IKZF1 subregions: chr7:50343867-50343961 (SEQ ID NO:3 or corresponding minus strand) and chr7:50343804-5033895 (SEQ ID NO:4 or corresponding minus strand)
   (3) IRF4 subregions chr6:392036-392145 (SEQ ID NO:5 or corresponding minus strand)
   (4) GRASP subregions: chr12:52399672-52399922, chr12:52400821-52401051 (SEQ ID NO:6 or corresponding minus strand), chr12:52401407-52401664 (SEQ ID NO:7 or corresponding minus strand) chr12:52400866-52400973 and Chr2:52401107-52401664, or
   (5) CAHM subregions: chr6:163834295-163834500 (SEQ ID NO:8 or corresponding minus strand), chr6:163834621-163834906, chr6:163834393-163834455 and chr6:163834393-163834519.

3. The method of claim 2, wherein said subregion is selected from SEQ ID NO.1 or SEQ ID NO.2, and SEQ ID NO.3, SEQ ID NO.4, SEQ ID NO.5, SEQ ID NO.6, SEQ ID NO.7, or SEQ ID NO.8 or corresponding minus strands.

4. The method of claim 2, said method comprising measuring the methylation of one or more cytosine residues selected from:

| (BCAT1) | | | |
|---|---|---|---|
| chr12:25101998 | chr12:25102003 | chr12:25102006 | chr12:25102009 |
| chr12:25102017 | chr12:25102022 | chr12:25102039 | chr12:25102048 |
| chr12:25102050 | chr12:25102053 | chr12:25102061 | chr12:25102063 |
| chr12:25102071 | chr112:25101921 | chr12:25101934 | chr12:25101943 |
| chr12:25101951 | chr12:25101962 | chr12:25101964 | chr12:25101970 |
| (GRASP) | | | |
| chr12:52399713 | chr12:52399731 | chr12:52399749 | chr12:52399783 |
| chr12:52399796 | chr12:52399808 | chr12:52399823 | chr12:52399835 |
| chr12:52399891 | chr12:52400847 | chr12:52400850 | chr12:52400859 |
| chr12:52400866 | chr12:52400869 | chr12:52400873 | chr12:52400881 |
| chr12:52400886 | chr12:52400893 | chr12:52400895 | chr12:52400899 |
| chr12:52400902 | chr12:52400907 | chr12:52400913 | chr12:52400919 |
| chr12:52400932 | chr12:52400938 | chr12:52400958 | chr12:52400962 |
| chr12:52400971 | chr12:52400973 | chr12:52400976 | chr12:52400998 |
| chr12:52401008 | chr12:52401010 | chr12:52401012 | chr12:52401016 |
| chr12:52401019 | chr12:52401025 | chr12:52401041 | chr12:52401044 |
| chr12:52401053 | chr12:52401060 | chr12:52401064 | chr12:52401092 |
| chr12:52401118 | chr12:52401438 | chr12:52401448 | chr12:52401460 |
| chr12:52401465 | chr12:52401474 | chr12:52401477 | chr12:52401479 |
| chr12:52401483 | chr12:52401504 | chr12:52401514 | chr12:52401523 |
| chr12:52401540 | chr12:52401553 | chr12:52401576 | chr12:52401588 |
| chr12:52401595 | chr12:52401599 | chr12:52401604 | chr12:52401606 |
| chr12:52401634 | chr12:52401640 | chr12:52401644 | chr12:52401659 |
| chr12:52401160 | chr12:52401165 | chr12:52401174 | chr12:52401177 |
| chr12:52401179 | chr12:52401183 | chr12:52401204 | chr12:52401215 |
| chr12:52401223 | chr12:52401240 | chr12:52401253 | chr12:52401288 |
| chr12:52401295 | chr12:52401299 | chr12:52401304 | chr12:52401334 |
| chr12:52401340 | chr12:52401344 | chr12:52401359 | |
| (CAHM) | | | |
| chr6:163834330 | chr6:163834332 | chr6:163834357 | |
| chr6:163834373 | chr6:163834384 | chr6:163834390 | |
| chr6:163834392 | chr6:163834406 | chr6:163834412 | |
| chr6:163834419 | chr6:163834443 | chr6:163834448 | |
| chr6:163834452 | chr6:163834464 | chr6:163834483 | |
| chr6:163834653 | chr6:163834660 | chr6:163834672 | |
| chr6:163834675 | chr6:163834678 | chr6:163834681 | |
| chr6:163834815 | chr6:163834824 | chr6:163834835 | |
| chr6:163834840 | chr6:163834853 | chr6:163834855 | |
| chr6:163834858 | chr6:163834863 | chr6:163834869 | |
| chr6:163834872 | | | |
| (IKZF1) | | | |
| chr7:50343869 | chr7:50343872 | chr7:50343883 | |
| chr7:50343889 | chr7:50343890 | chr7:50343897 | |
| chr7:50343907 | chr7:50343909 | chr7:50343914 | |
| chr7:50343934 | chr7:50343939 | chr7:50343950 | |
| chr7:50343959 | chr7:50343805 | chr7:50343822 | |

-continued

| | | |
|---|---|---|
| chr7:50343824 | chr7:50343826 | chr7:50343829 |
| chr7:50343831 | chr7:50343833 | chr7:50343838 |
| chr7:50343847 | chr7:50343850 | chr7:50343858 |
| chr7:50343864 | chr7:50343869 | chr7:50343872 |
| chr7:50343890 (IRF4) | | |
| chr6:392036 | chr6:392047 | chr6:392049 |
| chr6:392057 | chr6:392060 | chr6:392066 |
| chr6:392080 | chr6:392094 | chr6:392102 |
| chr6:392131 | | | or a corresponding cytosine at position n+1 on the opposite DNA strand.

5. The method of claim 1, wherein any one of said DNA regions exhibit a higher level of methylation relative to a control sample.

6. The method of claim 1, wherein any two or more of said DNA regions exhibits a higher level of methylation relative to a control sample.

7. The method of claim 1, wherein said neoplasm is an adenoma or an adenocarcinoma.

8. The method of claim 1, wherein said neoplasm is a colorectal neoplasm.

9. The method of claim 1, wherein said level of methylation is used to determine one or more probabilities of respective classifications of said large intestine neoplasm of said individual into one or more neoplastic categories selected from adenoma, stage I, stage II, stage III, or stage IV categories.

10. The method of claim 9, wherein said level of methylation is used to determine one or more probabilities of respective classifications of said large intestine neoplasm of said individual into one or more aggregates of fewer than five of said neoplastic categories.

11. The method of claim 1, wherein said level of methylation is used to determine a probability that said large intestine of said individual would be classified as non-neoplastic, based on comparison of said level of methylation relative to said corresponding measured levels of methylation and to corresponding measured levels of methylation from a population of individuals whose large intestines were classified as non-neoplastic.

12. The method of claim 10, wherein said aggregates include one or more of:
(i) one or more aggregates of fewer than five of said neoplastic categories and an aggregate of the non-neoplastic category with at least the adenoma category;
(ii) a pre-malignant neoplasm category consisting of an aggregate of the non-neoplastic and adenoma categories;
(iii) an early stage malignant neoplasm category consisting of an aggregate of the stage I and stage II categories;
(iv) a late stage malignant neoplasm category consisting of an aggregate of the stage III and stage IV categories; or
(v) the pre-malignant neoplasm category, the early stage malignant neoplasm category, and the late stage malignant neoplasm category.

* * * * *

UNITED STATES PATENT AND TRADEMARK OFFICE
CERTIFICATE OF CORRECTION

PATENT NO. : 10,941,449 B2
APPLICATION NO. : 14/401157
DATED : March 9, 2021
INVENTOR(S) : Lawrence Charles Lapointe et al.

It is certified that error appears in the above-identified patent and that said Letters Patent is hereby corrected as shown below:

On the Title Page

Right column, item (56), Other Publications, Line 2, delete "Lynphoblastic" and insert --Lymphoblastic--.

Right column, item (56), Other Publications, Line 8, delete "Cancer Cancer" and insert --Cancer--.

Right column, item (56), Other Publications, Line 19, delete "Claddification" and insert --Classification--.

Right column, item (56), Other Publications, Line 21, delete "cancder" and insert --cancer--.

Right column, item (57), ABSTRACT, Line 13, delete "adenocarcinosis" and insert --adenocarcinomas--.

On page 2, left column, item (56), Other Publications, Line 43, delete "DNA" and insert --individual DNA--.

In the Specification

In Column 1, Line 57, delete "adenÔcarcinomas" and insert --adenocarcinomas--.

In Column 4, Line 31, delete "nearby," and insert --nearby--.

In Column 4, Line 63, delete "N1 b" and insert --N1b--.

In Column 5, Line 5, delete "(T2): It" and insert --(T2). It--.

In Column 8, Line 4 (approx.), delete "chrl12" and insert --chr12--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,941,449 B2

In Column 8, Line 17 (approx.), delete "chrl 2" and insert --chr12--.

In Column 9, Line 38, delete "Stage 1" and insert --Stage I--.

In Column 9, Line 39, delete "Stage R" and insert --Stage II--.

In Column 9, Line 46, delete "Stage II-IV" and insert --Stage III-IV--.

In Column 9, Line 47, delete "Stage I-H" and insert --Stage I-II--.

In Column 9, Line 52, delete "log 10" and insert --log10--.

In Column 9, Line 55, delete "circles, Stage I" and insert --circles), Stage III--.

In Column 10, Line 12 (approx.), delete "cf" and insert --of--.

In Column 14, Line 21, delete "how," and insert --how--.

In Column 16, Line 32, delete "copying." and insert --copying--.

In Column 17, Line 62 (approx.), delete "chrl12" and insert --chr12--.

In Column 21, Line 28, delete "copieand" and insert --copies and--.

In Column 23, Line 53, delete "Methods Enzymol" and insert --Methods in Enzymology--.

In Column 23, Line 55, delete "et al Meth. Enzymol" and insert --et al., Methods in Enzymology--.

In Column 24, Line 3, delete "Res," and insert --Res.,--.

In Column 26, Line 12, delete "DNaseI" and insert --DNase I--.

In Column 28, Line 36, delete "bisulfate" and insert --bisulfite,--.

In Column 31, Line 5, delete "invention" and insert --invention.--.

In Column 31, Line 11, delete "MethylLight" and insert --MethyLight--.

In Column 31, Line 62, delete "rhodomine" and insert --rhodamine--.

In Column 32, Line 21, delete "bisulfate" and insert --bisulfite--.

In Column 32, Line 54, delete "bisulfate" and insert --bisulfite--.

In Column 32, Line 57, delete "1997)" and insert --1997--.

CERTIFICATE OF CORRECTION (continued)
U.S. Pat. No. 10,941,449 B2

In Column 34, Line 23, delete "bisulfate" and insert --bisulfite--.

In Column 35, Line 48, delete "spectrophometor" and insert --spectrophotometer--.

In Column 35, Line 56, delete "17.5" and insert --175--.

In Column 36, Line 10, delete "(Devon" and insert --(Devos--.

In Column 36, Line 11, delete "(Table 1)" and insert --(Table 1).--.

In Column 36, Line 14 (approx.), delete "model H" and insert --model II--.

In Column 36, Line 41 (approx.), delete "82.9.4" and insert --82.94--.

In Columns 37-38, Line 36 (approx.), delete "Foward" and insert --Forward--.

In Columns 37-38, Line 45 (approx.), delete "foward" and insert --forward--.

In Columns 37-38, Line 50 (approx.), delete "Foward" and insert --Forward--.

In Columns 37-38, Line 55 (approx.), delete "polymerse" and insert --polymerase--.

In Columns 37-38, Line 64 (approx.), delete "foward" and insert --forward--.

In Columns 39-40, Line 6 (approx.), delete "Foward" and insert --Forward--.

In Columns 39-40, Line 11 (approx.), delete "polymerse" and insert --polymerase--.

In Columns 39-40, Line 12 (approx.), delete "{BHQ1]" and insert --[BHQ1]--.

In Columns 39-40, Line 20 (approx.), delete "foward" and insert --forward--.

In Columns 39-40, Line 25 (approx.), delete "Foward" and insert --Forward--.

In Columns 39-40, Line 30 (approx.), delete "polymerse" and insert --polymerase--.

In Columns 39-40, Line 39 (approx.), delete "foward" and insert --forward--.

In Columns 39-40, Line 44 (approx.), delete "Foward" and insert --Forward--.

In Columns 39-40, Line 51 (approx.), delete "foward" and insert --forward--.

In Columns 39-40, Line 57 (approx.), delete "Foward" and insert --Forward--.

In Columns 39-40, Line 62 (approx.), delete "polymerse" and insert --polymerase--.

CERTIFICATE OF CORRECTION (continued)
U.S. Pat. No. 10,941,449 B2

In Columns 39-40, Line 71 (approx.), delete "foward" and insert --forward--.

In Columns 41-42, Line 5 (approx.), delete "Foward" and insert --Forward--.

In Columns 41-42, Line 10 (approx.), delete "polymerse" and insert --polymerase--.

In Columns 41-42, Line 19 (approx.), delete "foward" and insert --forward--.

In Columns 43-44, in Table, Line 19 (approx.), delete "(e.g." and insert --e.g.--.

In Columns 43-44, in Table, Line 20 (approx.), delete "((SEQ" and insert --(SEQ--.

In Columns 43-44, in Table, Line 37 (approx.), delete "(e.g." and insert --e.g.--.

In Columns 47-48, in Table, Line 11 (approx.), delete "(e.g." and insert --e.g.--.

In Column 51, Line 13, delete "(Clin." and insert --Clin.--.

In Column 51, Line 13, delete "0.1346" and insert --1346--.

In the Claims

In Column 83, Line 66, Claim 2, delete "Chr2" and insert --Chr12--.

In Column 84, Line 30, Claim 4, delete "chr112" and insert --chr12--.

SEQUENCE LISTING

```
<160> NUMBER OF SEQ ID NOS: 89

<210> SEQ ID NO 1
<211> LENGTH: 102
<212> TYPE: DNA
<213> ORGANISM: Artificial sequence
<220> FEATURE:
<223> OTHER INFORMATION: Synthetic construct

<400> SEQUENCE: 1
cagtgcccga ggcggcggcg agtacacgtg gcgggctgga ttgcagaccg gccctctcgc    60
ggcggagact cgcgacctag cggattgcat cagcaggaag ac                      102

<210> SEQ ID NO 2
<211> LENGTH: 87
<212> TYPE: DNA
<213> ORGANISM: Artificial sequence
<220> FEATURE:
<223> OTHER INFORMATION: Synthetic construct

<400> SEQUENCE: 2
agatcccaag ggtcgtagcc cctggccgtg tggaccgggt ctgcggctgc agagcgcggt    60
cccggctgca gcaagacctg gggcagt                                       87

<210> SEQ ID NO 3
<211> LENGTH: 95
<212> TYPE: DNA
<213> ORGANISM: Artificial sequence
<220> FEATURE:
<223> OTHER INFORMATION: Synthetic construct
```

<400> SEQUENCE: 3

| gacgacgcac cctctccgtg tcccgctctg cgcccttctg cgcgccccgc tccctgtacc | 60 |
| ggagcagcga tccgggaggc ggccgagagg tgcgc | 95 |

<210> SEQ ID NO 4
<211> LENGTH: 92
<212> TYPE: DNA
<213> ORGANISM: Artificial sequence
<220> FEATURE:
<223> OTHER INFORMATION: Synthetic construct

<400> SEQUENCE: 4

| ccggagttgc ggctgagacg cgcgccgcgc gagccggggg actcggcgac ggggcgggga | 60 |
| cgggacgacg caccctctcc gtgtcccgct ct | 92 |

<210> SEQ ID NO 5
<211> LENGTH: 110
<212> TYPE: DNA
<213> ORGANISM: Artificial sequence
<220> FEATURE:
<223> OTHER INFORMATION: Synthetic construct

<400> SEQUENCE: 5

| cgcctgccct ccgcgctcct gcgacggggt cgccacaagc tggacgggat gagctaaccg | 60 |
| gactgtcggg gccccaggag tggctgaggc ggggccgtcc aaggcaccca | 110 |

<210> SEQ ID NO 6
<211> LENGTH: 299
<212> TYPE: DNA
<213> ORGANISM: Artificial sequence
<220> FEATURE:
<223> OTHER INFORMATION: Synthetic construct

<400> SEQUENCE: 6

| caggaagctg cagcagaagg aggaggcggc ggccaccccg gaccccgccg cccggactcc | 60 |
| cgactcggaa gtcgcgcccg ccgctccggt cccgaccccg gaccccctg ccgcagccgc | 120 |
| caccctggg ccccagcgg acgagctgta cgcggcgctg gaggactatc accctgccga | 180 |
| gctgtaccgc gcgctcgccg tgtccggggg caccctgccc cgccgaaagg tgcgtccccc | 240 |
| gcccgccttc aggatctgct cagcccctct ccgactccct acagggcctg ctgactccg | 299 |

<210> SEQ ID NO 7
<211> LENGTH: 258
<212> TYPE: DNA
<213> ORGANISM: Artificial sequence
<220> FEATURE:
<223> OTHER INFORMATION: Synthetic construct

<400> SEQUENCE: 7

| gacagagaca gccccaggca agttgaaggt ccgagagccc ccggtgggag aagcgggccg | 60 |
| gtggctgcgc cgcgtgcgtt ctcactctga ggaagtgcgt ggggagccgc tgactccgga | 120 |
| tagcacaccc ttccgagggg actccccgat tcctgggctg ggggcctgcc gcctggcccc | 180 |
| acgtctgacg tacggggcgc gagggccact gctccctgga cttctgtcgg aaccggacgc | 240 |
| agtgggaggg gtcgcagg | 258 |

<210> SEQ ID NO 8
<211> LENGTH: 206
<212> TYPE: DNA
<213> ORGANISM: Artificial sequence
<220> FEATURE:
<223> OTHER INFORMATION: Synthetic construct

<400> SEQUENCE: 8

```
atctgtaaaa atgttgactt ctgcttttca gactacgcgc acagcctctt tatttcctac    60
tgcggcttca ttccctcacg gaacactgac gccatcgcga aggaagcatt tcgagcacga   120
ctgacgctcc ccttattatt tgctaagccg ctgcgctcgg gtctggctac gatttgcttt   180
cagaataacg ggaaggtgca acaaga                                        206
```

<210> SEQ ID NO 9
<211> LENGTH: 27
<212> TYPE: DNA
<213> ORGANISM: Artificial sequence
<220> FEATURE:
<223> OTHER INFORMATION: Synthetic construct

<400> SEQUENCE: 9

```
gaaggaagta tttcgagtac gattgac                                        27
```

<210> SEQ ID NO 10
<211> LENGTH: 19
<212> TYPE: DNA
<213> ORGANISM: Artificial sequence
<220> FEATURE:
<223> OTHER INFORMATION: Synthetic construct

<400> SEQUENCE: 10

```
cccgaacgca acgacttaa                                                 19
```

<210> SEQ ID NO 11
<211> LENGTH: 17
<212> TYPE: DNA
<213> ORGANISM: Artificial sequence
<220> FEATURE:
<223> OTHER INFORMATION: Synthetic construct

<400> SEQUENCE: 11

```
cggaagtcgc gttcgtc                                                   17
```

<210> SEQ ID NO 12
<211> LENGTH: 20
<212> TYPE: DNA
<213> ORGANISM: Artificial sequence
<220> FEATURE:
<223> OTHER INFORMATION: Synthetic construct

<400> SEQUENCE: 12

```
gcgtacaact cgtccgctaa                                                20
```

<210> SEQ ID NO 13
<211> LENGTH: 28
<212> TYPE: DNA
<213> ORGANISM: Artificial sequence
<220> FEATURE:
<223> OTHER INFORMATION: Synthetic construct

<400> SEQUENCE: 13

```
ttcgatttcg ggatttttg tcgtagtc                                        28
```

<210> SEQ ID NO 14
<211> LENGTH: 20
<212> TYPE: DNA
<213> ORGANISM: Artificial sequence

```
<220> FEATURE:
<223> OTHER INFORMATION: Synthetic construct

<400> SEQUENCE: 14
tgggtgtttt ggacggtttc                                              20

<210> SEQ ID NO 15
<211> LENGTH: 15
<212> TYPE: DNA
<213> ORGANISM: Artificial sequence
<220> FEATURE:
<223> OTHER INFORMATION: Synthetic construct

<400> SEQUENCE: 15
cgcctaccct ccgcg                                                   15

<210> SEQ ID NO 16
<211> LENGTH: 26
<212> TYPE: DNA
<213> ORGANISM: Artificial sequence
<220> FEATURE:
<223> OTHER INFORMATION: Synthetic construct

<400> SEQUENCE: 16
tcgtttagtt tgtggcgatt tcgtcg                                       26

<210> SEQ ID NO 17
<211> LENGTH: 29
<212> TYPE: DNA
<213> ORGANISM: Artificial sequence
<220> FEATURE:
<223> OTHER INFORMATION: Synthetic construct

<400> SEQUENCE: 17 gttttttgt tgatgtaatt cgttaggtc                                     29

<210> SEQ ID NO 18
<211> LENGTH: 20
<212> TYPE: DNA
<213> ORGANISM: Artificial sequence
<220> FEATURE:
<223> OTHER INFORMATION: Synthetic construct

<400> SEQUENCE: 18
caatacccga aacgacgacg                                              20

<210> SEQ ID NO 19
<211> LENGTH: 21
<212> TYPE: DNA
<213> ORGANISM: Artificial sequence
<220> FEATURE:
<223> OTHER INFORMATION: Synthetic construct

<400> SEQUENCE: 19
ttcgtcgcga gagggtcggt t                                            21

<210> SEQ ID NO 20
<211> LENGTH: 24
<212> TYPE: DNA
<213> ORGANISM: Artificial sequence
<220> FEATURE:
<223> OTHER INFORMATION: Synthetic construct

<400> SEQUENCE: 20
gacgacgtat tttttcgtg tttc                                          24
```

```
<210> SEQ ID NO 21
<211> LENGTH: 16
<212> TYPE: DNA
<213> ORGANISM: Artificial sequence
<220> FEATURE:
<223> OTHER INFORMATION: Synthetic construct

<400> SEQUENCE: 21
gcgcacctct cgaccg                                                     16

<210> SEQ ID NO 22
<211> LENGTH: 21
<212> TYPE: DNA
<213> ORGANISM: Artificial sequence
<220> FEATURE:
<223> OTHER INFORMATION: Synthetic construct

<400> SEQUENCE: 22
taagagtaat aatggatgga t                                               21

<210> SEQ ID NO 23
<211> LENGTH: 17
<212> TYPE: DNA
<213> ORGANISM: Artificial sequence
<220> FEATURE:
<223> OTHER INFORMATION: Synthetic construct

<400> SEQUENCE: 23
cctcccatct cccttcc                                                    17

<210> SEQ ID NO 24
<211> LENGTH: 25
<212> TYPE: DNA
<213> ORGANISM: Artificial sequence
<220> FEATURE:
<223> OTHER INFORMATION: Synthetic construct

<400> SEQUENCE: 24
atggatgaag aaagaaagga tgagt                                           25

<210> SEQ ID NO 25
<211> LENGTH: 24
<212> TYPE: DNA
<213> ORGANISM: Artificial sequence
<220> FEATURE:
<223> OTHER INFORMATION: Synthetic construct

<400> SEQUENCE: 25
gtgatggagg aggtttagta agtt                                            24

<210> SEQ ID NO 26
<211> LENGTH: 25
<212> TYPE: DNA
<213> ORGANISM: Artificial sequence
<220> FEATURE:
<223> OTHER INFORMATION: Synthetic construct

<400> SEQUENCE: 26
ccaataaaac ctactcctcc cttaa                                           25

<210> SEQ ID NO 27
<211> LENGTH: 30
<212> TYPE: DNA
<213> ORGANISM: Artificial sequence
<220> FEATURE:
<223> OTHER INFORMATION: Synthetic construct
```

<400> SEQUENCE: 27
accaccaccc aacacacaat aacaaacaca                                30

<210> SEQ ID NO 28
<211> LENGTH: 102
<212> TYPE: DNA
<213> ORGANISM: Artificial sequence
<220> FEATURE:
<223> OTHER INFORMATION: Synthetic construct

<400> SEQUENCE: 28
tagtgttcga ggcggcggcg agtatacgtg gcgggttgga ttgtagatcg gttttttcgc    60
ggcggagatt cgcgatttag cggattgtat tagtaggaag at                     102

<210> SEQ ID NO 29
<211> LENGTH: 102
<212> TYPE: DNA
<213> ORGANISM: Artificial sequence
<220> FEATURE:
<223> OTHER INFORMATION: Synthetic construct

<400> SEQUENCE: 29
gtcacgggct ccgccgccgc tcatgtgcac cgcccgacct aacgtctggc cgggagagcg    60
ccgcctctga gcgctggatc gcctaacgta gtcgtccttc tg                     102

<210> SEQ ID NO 30
<211> LENGTH: 102
<212> TYPE: DNA
<213> ORGANISM: Artificial sequence
<220> FEATURE:
<223> OTHER INFORMATION: Synthetic construct

<400> SEQUENCE: 30
gttatgggct tgctgctgc ttatgtgcat tgcttgattt aatgtttggc tgggagagcg     60
ctgcttttga gcgctggatt gcttaatgta gttgtttttt tg                     102

<210> SEQ ID NO 31
<211> LENGTH: 29
<212> TYPE: DNA
<213> ORGANISM: Artificial sequence
<220> FEATURE:
<223> OTHER INFORMATION: Synthetic construct

<400> SEQUENCE: 31 gttttttttgt tgatgtaatt cgttaggtc                                   29

<210> SEQ ID NO 32
<211> LENGTH: 20
<212> TYPE: DNA
<213> ORGANISM: Artificial sequence
<220> FEATURE:
<223> OTHER INFORMATION: Synthetic construct

<400> SEQUENCE: 32
caatacccga aacgacgacg                                              20

<210> SEQ ID NO 33
<211> LENGTH: 21
<212> TYPE: DNA
<213> ORGANISM: Artificial sequence
<220> FEATURE:
<223> OTHER INFORMATION: Synthetic construct

```
<400> SEQUENCE: 33
ttcgtcgcga gagggtcggt t                                              21

<210> SEQ ID NO 34
<211> LENGTH: 26
<212> TYPE: DNA
<213> ORGANISM: Artificial sequence
<220> FEATURE:
<223> OTHER INFORMATION: Synthetic construct

<400> SEQUENCE: 34
tttttgttga tgtaattcgt taggtc                                         26

<210> SEQ ID NO 35
<211> LENGTH: 20
<212> TYPE: DNA
<213> ORGANISM: Artificial sequence
<220> FEATURE:
<223> OTHER INFORMATION: Synthetic construct

<400> SEQUENCE: 35
attacaaacc gaccctctcg                                                20

<210> SEQ ID NO 36
<211> LENGTH: 19
<212> TYPE: DNA
<213> ORGANISM: Artificial sequence
<220> FEATURE:
<223> OTHER INFORMATION: Synthetic construct

<400> SEQUENCE: 36
agatcccaag ggtcgtagc                                                 19

<210> SEQ ID NO 37
<211> LENGTH: 18
<212> TYPE: DNA
<213> ORGANISM: Artificial sequence
<220> FEATURE:
<223> OTHER INFORMATION: Synthetic construct

<400> SEQUENCE: 37
actgccccag gtcttgct                                                  18

<210> SEQ ID NO 38
<211> LENGTH: 87
<212> TYPE: DNA
<213> ORGANISM: Artificial sequence
<220> FEATURE:
<223> OTHER INFORMATION: Synthetic construct

<400> SEQUENCE: 38
tctagggttc ccagcatcgg ggaccggcac acctggccca gacgccgacg tctcgcgcca    60
gggccgacgt cgttctggac cccgtca                                        87

<210> SEQ ID NO 39
<211> LENGTH: 95
<212> TYPE: DNA
<213> ORGANISM: Artificial sequence
<220> FEATURE:
<223> OTHER INFORMATION: Synthetic construct

<400> SEQUENCE: 39
gacgacgtat ttttttcgtg tttcgttttg cgttttttg cgcgtttcgt tttttgtatc     60
ggagtagcga ttcgggaggc ggtcgagagg tgcgt                               95
```

```
<210> SEQ ID NO 40
<211> LENGTH: 24
<212> TYPE: DNA
<213> ORGANISM: Artificial sequence
<220> FEATURE:
<223> OTHER INFORMATION: Synthetic construct

<400> SEQUENCE: 40
gacgacgtat tttttcgtg tttc                                              24

<210> SEQ ID NO 41
<211> LENGTH: 15
<212> TYPE: DNA
<213> ORGANISM: Artificial sequence
<220> FEATURE:
<223> OTHER INFORMATION: Synthetic construct

<400> SEQUENCE: 41
gcgcacctct cgacc                                                       15

<210> SEQ ID NO 42
<211> LENGTH: 26
<212> TYPE: DNA
<213> ORGANISM: Artificial sequence
<220> FEATURE:
<223> OTHER INFORMATION: Synthetic construct

<400> SEQUENCE: 42
tttgtatcgg agtagcgatt cgggag                                           26

<210> SEQ ID NO 43
<211> LENGTH: 95
<212> TYPE: DNA
<213> ORGANISM: Artificial sequence
<220> FEATURE:
<223> OTHER INFORMATION: Synthetic construct

<400> SEQUENCE: 43
ctgctgcgtg ggagaggcac agggcgagac gcgggaagac gcgcggggcg agggacatgg       60
cctcgtcgct aggccctccg ccggctctcc acgcg                                 95

<210> SEQ ID NO 44
<211> LENGTH: 95
<212> TYPE: DNA
<213> ORGANISM: Artificial sequence
<220> FEATURE:
<223> OTHER INFORMATION: Synthetic construct

<400> SEQUENCE: 44
ttgctgcgtg ggagaggcat agggcgagat gcgggaagat gcgcggggcg agggatatgg       60
ctttgttgct aggcttttg ctggcttttt atgcg                                  95

<210> SEQ ID NO 45
<211> LENGTH: 17
<212> TYPE: DNA
<213> ORGANISM: Artificial sequence
<220> FEATURE:
<223> OTHER INFORMATION: Synthetic construct

<400> SEQUENCE: 45
ggagttgcgg ctgagac                                                     17
```

```
<210> SEQ ID NO 46
<211> LENGTH: 17
<212> TYPE: DNA
<213> ORGANISM: Artificial sequence
<220> FEATURE:
<223> OTHER INFORMATION: Synthetic construct

<400> SEQUENCE: 46
agagcgggac acggaga                                                    17

<210> SEQ ID NO 47
<211> LENGTH: 92
<212> TYPE: DNA
<213> ORGANISM: Artificial sequence
<220> FEATURE:
<223> OTHER INFORMATION: Synthetic construct

<400> SEQUENCE: 47
ggcctcaacg ccgactctgc gcgcggcgcg ctcggccccc tgagccgctg ccccgcccct     60
gccctgctgc gtgggagagg cacagggcga ga                                   92

<210> SEQ ID NO 48
<211> LENGTH: 110
<212> TYPE: DNA
<213> ORGANISM: Artificial sequence
<220> FEATURE:
<223> OTHER INFORMATION: Synthetic construct

<400> SEQUENCE: 48
cgtttgtttt tcgcgttttt gcgacggggt cgttataagt tggacgggat gagttaatcg     60
gattgtcggg gttttaggag tggttgaggc ggggtcgttt aaggtattta                110

<210> SEQ ID NO 49
<211> LENGTH: 17
<212> TYPE: DNA
<213> ORGANISM: Artificial sequence
<220> FEATURE:
<223> OTHER INFORMATION: Synthetic construct

<400> SEQUENCE: 49
gtttttgcga cggggtc                                                    17

<210> SEQ ID NO 50
<211> LENGTH: 18
<212> TYPE: DNA
<213> ORGANISM: Artificial sequence
<220> FEATURE:
<223> OTHER INFORMATION: Synthetic construct

<400> SEQUENCE: 50 taaaacccg acaatccg                                                    18

<210> SEQ ID NO 51
<211> LENGTH: 110
<212> TYPE: DNA
<213> ORGANISM: Artificial sequence
<220> FEATURE:
<223> OTHER INFORMATION: Synthetic construct

<400> SEQUENCE: 51
gcggacggga ggcgcgagga cgctgcccca gcggtgttcg acctgcccta ctcgattggc     60
ctgacagccc cggggtcctc accgactccg ccccggcagg ttccgtgggt                110
```

```
<210> SEQ ID NO 52
<211> LENGTH: 110
<212> TYPE: DNA
<213> ORGANISM: Artificial sequence
<220> FEATURE:
<223> OTHER INFORMATION: Synthetic construct

<400> SEQUENCE: 52
gcggatggga ggcgcgagga tgctgcttta gcggtgtttg atttgcttta tttgattggc    60
ttgatagctt tggggttttt attgattttg ctttggcagg ttttgtgggt                110

<210> SEQ ID NO 53
<211> LENGTH: 20
<212> TYPE: DNA
<213> ORGANISM: Artificial sequence
<220> FEATURE:
<223> OTHER INFORMATION: Synthetic construct

<400> SEQUENCE: 53
tgggtgtttt ggacggtttc                                                 20

<210> SEQ ID NO 54
<211> LENGTH: 27
<212> TYPE: DNA
<213> ORGANISM: Artificial sequence
<220> FEATURE:
<223> OTHER INFORMATION: Synthetic construct

<400> SEQUENCE: 54
tagttatttt tggggtttcg atagttc                                         27

<210> SEQ ID NO 55
<211> LENGTH: 15
<212> TYPE: DNA
<213> ORGANISM: Artificial sequence
<220> FEATURE:
<223> OTHER INFORMATION: Synthetic construct

<400> SEQUENCE: 55
cgcctaccct ccgcg                                                      15

<210> SEQ ID NO 56
<211> LENGTH: 26
<212> TYPE: DNA
<213> ORGANISM: Artificial sequence
<220> FEATURE:
<223> OTHER INFORMATION: Synthetic construct

<400> SEQUENCE: 56
tcgtttagtt tgtggcgatt tcgtcg                                          26

<210> SEQ ID NO 57
<211> LENGTH: 299
<212> TYPE: DNA
<213> ORGANISM: Artificial sequence
<220> FEATURE:
<223> OTHER INFORMATION: Synthetic construct

<400> SEQUENCE: 57
taggaagttg tagtagaagg aggaggcggc ggttatttcg gatttcgtcg ttcggatttt    60
cgattcggaa gtcgcgttcg tcgtttcggt ttcgatttcg ggatttttg tcgtagtcgt    120 tatttttggg tttttagcgg acgagttgta cgcggcgttg gaggattatt attttgtcga    180
```

```
gttgtatcgc gcgttcgtcg tgttcggggg tattttgttt cgtcgaaagg tgcgtttttc    240
gttcgttttt aggatttgtt tagttttttt tcgattttt ataggggttg ttgatttcg      299
```

<210> SEQ ID NO 58
<211> LENGTH: 17
<212> TYPE: DNA
<213> ORGANISM: Artificial sequence
<220> FEATURE:
<223> OTHER INFORMATION: Synthetic construct

<400> SEQUENCE: 58

```
cggaagtcgc gttcgtc                                                    17
```

<210> SEQ ID NO 59
<211> LENGTH: 20
<212> TYPE: DNA
<213> ORGANISM: Artificial sequence
<220> FEATURE:
<223> OTHER INFORMATION: Synthetic construct

<400> SEQUENCE: 59

```
gcgtacaact cgtccgctaa                                                 20
```

<210> SEQ ID NO 60
<211> LENGTH: 28
<212> TYPE: DNA
<213> ORGANISM: Artificial sequence
<220> FEATURE:
<223> OTHER INFORMATION: Synthetic construct

<400> SEQUENCE: 60

```
ttcgatttcg ggatttttg tcgtagtc                                         28
```

<210> SEQ ID NO 61
<211> LENGTH: 20
<212> TYPE: DNA
<213> ORGANISM: Artificial sequence
<220> FEATURE:
<223> OTHER INFORMATION: Synthetic construct

<400> SEQUENCE: 61

```
cggatttcg attcggaagt                                                  20
```

<210> SEQ ID NO 62
<211> LENGTH: 298
<212> TYPE: DNA
<213> ORGANISM: Artificial sequence
<220> FEATURE:
<223> OTHER INFORMATION: Synthetic construct

<400> SEQUENCE: 62

```
gtccttcgac gtcgtcttcc tcctccgccg ccggtggggc ctggggcggc gggcctgagg    60
gctgagcctc agcgcgggcg gcgaggccag ggctgggggcc ctgggggacg gcgtcggcgg   120 tgggggacccg ggggtcgcct gctcgacatg cgccgcgacc tcctgatagt gggacggctc   180
gacatggcgc gcgagcggca caggcccccg tgggacgggg cggctttcca cgcaggggggc   240 gggcggaagt cctagacgag tcggggagag gctgagggat gtcccggacg actgaggc      298
```

<210> SEQ ID NO 63
<211> LENGTH: 298
<212> TYPE: DNA
<213> ORGANISM: Artificial sequence
<220> FEATURE:
<223> OTHER INFORMATION: Synthetic construct

```
<400> SEQUENCE: 63 gtttttttgat gttgtttttt tttttttgctg ctggtggggc ttggggcggc gggcttgagg    60
gctgagcttt agcgcgggcg gcgaggctag ggctggggct ttgggggatg gcgttggcgg    120
tggggatttg ggggttgctt gcttgatatg cgctgcgatt ttttgatagt gggatggctt    180
gatatggcgc gcgagcggca taggcttttg tgggatgggg cggcttttta tgcagggggc    240
gggcggaagt tttagatgag ttggggagag gctgagggat gttttggatg attgaggc     298

<210> SEQ ID NO 64
<211> LENGTH: 20
<212> TYPE: DNA
<213> ORGANISM: Artificial sequence
<220> FEATURE:
<223> OTHER INFORMATION: Synthetic construct

<400> SEQUENCE: 64
ggtagggtgt tttcggatac                                                  20

<210> SEQ ID NO 65
<211> LENGTH: 21
<212> TYPE: DNA
<213> ORGANISM: Artificial sequence
<220> FEATURE:
<223> OTHER INFORMATION: Synthetic construct

<400> SEQUENCE: 65
aacgaacgaa ctatacgcga c                                                21

<210> SEQ ID NO 66
<211> LENGTH: 258
<212> TYPE: DNA
<213> ORGANISM: Artificial sequence
<220> FEATURE:
<223> OTHER INFORMATION: Synthetic construct

<400> SEQUENCE: 66
gatagagata gttttaggta agttgaaggt tcgagagttt tcggtgggag aagcgggtcg    60
gtggttgcgt cgcgtgcgtt tttattttga ggaagtgcgt ggggagtcgt tgatttcgga    120
tagtatattt tttcgagggg attttttcgat ttttggttg ggggtttgtc gtttggtttt    180
acgtttgacg tacggggcgc gagggttatt gttttttgga ttttttgtcgg aatcggacgt    240 agtgggaggg gtcgtagg                                                    258

<210> SEQ ID NO 67
<211> LENGTH: 258
<212> TYPE: DNA
<213> ORGANISM: Artificial sequence
<220> FEATURE:
<223> OTHER INFORMATION: Synthetic construct

<400> SEQUENCE: 67
ctgtctctgt cggggtccgt tcaacttcca ggctctcggg ggccaccctc ttcgcccggc    60
caccgacgcg gcgcacgcaa gagtgagact ccttcacgca cccctcggcg actgaggcct    120
atcgtgtggg aaggctcccc tgaggggcta aggacccgac cccggacgg cggaccgggg     180 tgcagactgc atgccccgcg ctcccggtga cgagggacct gaagacagcc ttggcctgcg    240
tcaccctccc cagcgtcc                                                    258
```

<210> SEQ ID NO 68
<211> LENGTH: 258
<212> TYPE: DNA
<213> ORGANISM: Artificial sequence
<220> FEATURE:
<223> OTHER INFORMATION: Synthetic construct

<400> SEQUENCE: 68 ttgttttttgt tggggtttgt ttaatttttta ggcttttggg ggctattttt tttgcttggc    60
tattgatgcg gcgcatgcaa gagtgagatt tttttatgca ttttttggcg attgaggctt   120
attgtgtggg aaggcttttt tgaggggcta aggatttgat ttttggatgg cggattgggg   180
tgcagattgc atgctttgcg cttttggtga tgagggattt gaagatagct ttggcttgcg   240 ttatttttttt tagcgttt                                                 258

<210> SEQ ID NO 69
<211> LENGTH: 21
<212> TYPE: DNA
<213> ORGANISM: Artificial sequence
<220> FEATURE:
<223> OTHER INFORMATION: Synthetic construct

<400> SEQUENCE: 69
cggagttagc ggttttttac g                                               21

<210> SEQ ID NO 70
<211> LENGTH: 20
<212> TYPE: DNA
<213> ORGANISM: Artificial sequence
<220> FEATURE:
<223> OTHER INFORMATION: Synthetic construct

<400> SEQUENCE: 70
cgataaaaaa aacgaaccga                                                 20

<210> SEQ ID NO 71
<211> LENGTH: 20
<212> TYPE: DNA
<213> ORGANISM: Artificial sequence
<220> FEATURE:
<223> OTHER INFORMATION: Synthetic construct

<400> SEQUENCE: 71
agagtgagaa cgtacgcggc                                                 20

<210> SEQ ID NO 72
<211> LENGTH: 258
<212> TYPE: DNA
<213> ORGANISM: Artificial sequence
<220> FEATURE:
<223> OTHER INFORMATION: Synthetic construct

<400> SEQUENCE: 72
gacagagaca gccccaggca agttgaaggt ccgagagccc ccggtgggag aagcgggccg     60
gtggctgcgc cgcgtgcgtt ctcactctga ggaagtgcgt ggggagccgc tgactccgga   120
tagcacaccc ttccgagggg actccccgat tcctgggctg ggggcctgcc gcctggcccc   180
acgtctgacg tacgggcgc gagggccact gctccctgga cttctgtcgg aaccggacgc   240
agtgggaggg gtcgcagg                                                  258

```
<210> SEQ ID NO 73
<211> LENGTH: 19
<212> TYPE: DNA
<213> ORGANISM: Artificial sequence
<220> FEATURE:
<223> OTHER INFORMATION: Synthetic construct

<400> SEQUENCE: 73
caagttgaag gtccgagag                                               19

<210> SEQ ID NO 74
<211> LENGTH: 20
<212> TYPE: DNA
<213> ORGANISM: Artificial sequence
<220> FEATURE:
<223> OTHER INFORMATION: Synthetic construct

<400> SEQUENCE: 74
cgcacttcct cagagtgaga                                              20

<210> SEQ ID NO 75
<211> LENGTH: 258
<212> TYPE: DNA
<213> ORGANISM: Artificial sequence
<220> FEATURE:
<223> OTHER INFORMATION: Synthetic construct

<400> SEQUENCE: 75
ctgtctctgt cggggtccgt tcaacttcca ggctctcggg ggccaccctc ttcgcccggc     60
caccgacgcg gcgcacgcaa gagtgagact ccttcacgca ccctcggcg actgaggcct    120 atcgtgtggg aaggctcccc tgaggggcta aggacccgac ccccggacgg cggaccgggg   180
tgcagactgc atgccccgcg ctcccggtga cgagggacct gaagacagcc ttggcctgcg   240
tcaccctccc cagcgtcc                                                258

<210> SEQ ID NO 76
<211> LENGTH: 206
<212> TYPE: DNA
<213> ORGANISM: Artificial sequence
<220> FEATURE:
<223> OTHER INFORMATION: Synthetic construct

<400> SEQUENCE: 76
atttgtaaaa atgttgattt ttgtttttta gattacgcgt atagtttttt tattttttat     60 tgcggttttta ttttttttacg gaatattgac gttatcgcga aggaagtatt tcgagtacga  120
ttgacgtttt ttttattatt tgttaagtcg ttgcgttcgg gtttggttac gatttgtttt   180
tagaataacg ggaaggtgta ataaga                                       206

<210> SEQ ID NO 77
<211> LENGTH: 28
<212> TYPE: DNA
<213> ORGANISM: Artificial sequence
<220> FEATURE:
<223> OTHER INFORMATION: Synthetic construct

<400> SEQUENCE: 77
gaaggaagta tttcgagtac gattgacc                                     28

<210> SEQ ID NO 78
<211> LENGTH: 19
<212> TYPE: DNA
<213> ORGANISM: Artificial sequence
```

```
<220> FEATURE:
<223> OTHER INFORMATION: Synthetic construct

<400> SEQUENCE: 78
cccgaacgca acgacttaa                                                19

<210> SEQ ID NO 79
<211> LENGTH: 28
<212> TYPE: DNA
<213> ORGANISM: Artificial sequence
<220> FEATURE:
<223> OTHER INFORMATION: Synthetic construct

<400> SEQUENCE: 79
gcctctaaaa aaacgatctt attacacc                                      28

<210> SEQ ID NO 80
<211> LENGTH: 206
<212> TYPE: DNA
<213> ORGANISM: Artificial sequence
<220> FEATURE:
<223> OTHER INFORMATION: Synthetic construct

<400> SEQUENCE: 80
tagacatttt tacaactgaa gacgaaaagt ctgatgcgcg tgtcggagaa ataaaggatg    60
acgccgaagt aagggagtgc cttgtgactg cggtagcgct tccttcgtaa agctcgtgct   120
gactgcgagg ggaataataa acgattcggc gacgcgagcc cagaccgatg ctaaacgaaa   180
gtcttattgc ccttccacgt tgttct                                       206

<210> SEQ ID NO 81
<211> LENGTH: 206
<212> TYPE: DNA
<213> ORGANISM: Artificial sequence
<220> FEATURE:
<223> OTHER INFORMATION: Synthetic construct

<400> SEQUENCE: 81
tagatatttt tataattgaa gatgaaaagt ttgatgcgcg tgttggagaa ataaaggatg    60
atgctgaagt aagggagtgc tttgtgattg cggtagcgct ttttttgtaa agcttgtgct   120
gattgcgagg ggaataataa atgatttggc gatgcgagct tagattgatg ctaaatgaaa   180
gttttattgc ttttttatgt tgtttt                                       206

<210> SEQ ID NO 82
<211> LENGTH: 18
<212> TYPE: DNA
<213> ORGANISM: Artificial sequence
<220> FEATURE:
<223> OTHER INFORMATION: Synthetic construct

<400> SEQUENCE: 82
gaaacactaa cgccatcg                                                 18

<210> SEQ ID NO 83
<211> LENGTH: 21
<212> TYPE: DNA
<213> ORGANISM: Artificial sequence
<220> FEATURE:
<223> OTHER INFORMATION: Synthetic construct

<400> SEQUENCE: 83
cgtagttaga ttcgagcgta g                                             21
```

-continued

```
<210> SEQ ID NO 84
<211> LENGTH: 25
<212> TYPE: DNA
<213> ORGANISM: Artificial sequence
<220> FEATURE:
<223> OTHER INFORMATION: Synthetic construct

<400> SEQUENCE: 84
aggggagcgt tagtcgtgtt cgaaa                                          25

<210> SEQ ID NO 85
<211> LENGTH: 285
<212> TYPE: DNA
<213> ORGANISM: Artificial sequence
<220> FEATURE:
<223> OTHER INFORMATION: Synthetic construct

<400> SEQUENCE: 85
cggcacgacg aaaggtcgga gagtcgttta gtgcttgtgg ctttcttcgg tgccgccgct    60
gccctccccg cagcgcgcac gaagggagcc gctgttccgc cctcggcccg cgcggccggc   120
tcccgcgggc cgcgtctcag ggcgtctccg cctgcgcgcg cgtgcgcgga gcttttcgga   180
gtttgagaat aggagccgag agggcggggt ggaggcgggg cgtcggttct gggcgcggca   240
ccgcccgggc tgccggttcc tttcgggtgg tcgggaggct ggcac                   285

<210> SEQ ID NO 86
<211> LENGTH: 285
<212> TYPE: DNA
<213> ORGANISM: Artificial sequence
<220> FEATURE:
<223> OTHER INFORMATION: Synthetic construct

<400> SEQUENCE: 86
tggcatgatg aaaggttgga gagttgttta gtgcttgtgg ctttttttgg tgctgctgct    60 gcttttttg cagcgcgcat gaagggagct gctgttttgc ttttggcttg cgcggctggc   120
ttttgcgggc tgcgttttag ggcgtttttg cttgcgcgc tgtgcgcgga gcttttcgga   180
gtttgagaat aggagctgag agggcggggt ggaggcgggg cgttggtttt gggcgcggca   240
ttgcttgggc tgctggtttt ttttgggtgg ttgggaggct ggcat                   285

<210> SEQ ID NO 87
<211> LENGTH: 20
<212> TYPE: DNA
<213> ORGANISM: Artificial sequence
<220> FEATURE:
<223> OTHER INFORMATION: Synthetic construct

<400> SEQUENCE: 87 gttttttcg gcgataaagc                                                 20

<210> SEQ ID NO 88
<211> LENGTH: 20
<212> TYPE: DNA
<213> ORGANISM: Artificial sequence
<220> FEATURE:
<223> OTHER INFORMATION: Synthetic construct

<400> SEQUENCE: 88
cgcctctacg aaactctacg                                                20
```

```
<210> SEQ ID NO 89
<211> LENGTH: 18
<212> TYPE: DNA
<213> ORGANISM: Artificial sequence
<220> FEATURE:
<223> OTHER INFORMATION: Synthetic construct

<400> SEQUENCE: 89
cgtcggtcga gggcgttc                                                    18
```